US006184011B1

(12) United States Patent
Siegel et al.

(10) Patent No.: US 6,184,011 B1
(45) Date of Patent: Feb. 6, 2001

(54) METHOD OF RELEASING SOLID MATRIX AFFINITY ADSORBED PARTICULATES

(75) Inventors: Daniel L. Siegel, Rehovot; Oded Shoseyov, Karme Yosef, both of (IL)

(73) Assignees: CBD Technologies, LTD, Rehovot; Yissum R&D Company of the Hebrew University, Jerusalem, both of (IL)

(*) Notice: Under 35 U.S.C. 154(b), the term of this patent shall be extended for 0 days.

(21) Appl. No.: 09/273,268

(22) Filed: Mar. 22, 1999

(51) Int. Cl.[7] .................... C12N 13/00; C12N 15/00; C12N 1/02; G01N 33/543; G01N 33/544

(52) U.S. Cl. .................... 435/173.1; 435/173.9; 435/174; 435/179; 435/261; 435/262; 435/262.5; 435/263; 435/264; 435/267; 435/273; 435/274; 435/275; 435/308.1; 435/961; 436/518; 436/528; 436/529; 436/520; 436/823; 436/824

(58) Field of Search .................... 436/518, 528, 436/529, 530, 823, 824; 435/173.1, 173.9, 174, 179, 261, 262, 262.5, 263, 264, 267, 273–275, 308.1, 961

(56) References Cited

U.S. PATENT DOCUMENTS

| 4,338,398 | * | 7/1982 | Yoneyama ............... 435/95 |
| 4,732,811 | | 3/1988 | Margel . |
| 4,861,705 | | 8/1989 | Margel . |
| 4,994,390 | * | 2/1991 | Wiarr ................... 435/262 |
| 5,081,030 | | 1/1992 | Civin . |
| 5,122,449 | * | 6/1992 | Gilbert et al. ............. 435/5 |
| 5,217,905 | * | 6/1993 | Marchand et al. .......... 436/518 |
| 5,457,046 | * | 10/1995 | Woldike et al. ........... 435/209 |
| 5,656,490 | * | 8/1997 | Wyatt et al. ............. 435/281 |
| 5,821,358 | | 10/1998 | Gilkes et al. . |
| 5,872,091 | * | 2/1999 | Cuperus et al. ........... 510/300 |
| 5,888,533 | * | 3/1999 | Dunn .................... 424/423 |

* cited by examiner

Primary Examiner—Christopher L. Chin
Assistant Examiner—Pensee T. Do

(57) ABSTRACT

A method of releasing particulates from a solid matrix is provided. The method is effected adding to the solid matrix a degrading enzyme capable of degrading the solid matrix, to thereby release the particulates from the solid matrix.

43 Claims, 2 Drawing Sheets

METHOD OF RELEASING SOLID MATRIX AFFINITY ADSORBED PARTICULATES

FIELD AND BACKGROUND OF THE INVENTION

The present invention relates to a method of releasing solid matrix affinity adsorbed particulates by enzymatically degrading the solid matrix to which the particulates are adsorbed. More particularly, the present invention relates to a method of releasing particulates, such as viruses, cells or fragments thereof, which are affinity adsorbed on a polysaccharide solid matrix, by enzymatically degrading the polysaccharide solid matrix to which the particulates are adsorbed with a polysaccharidase.

The need for efficient affinity adsorption and release methods:

There is a tremendous effort being made to develop rapid cell testing and separation methods to meet the needs of the food, medical, environmental and veterinary industries.

The food industry, for example, needs rapid microbial testing to approve or reject raw materials and determine whether or not to release a held batch of product. Furthermore, with the increasing implementation of hazard analysis and critical control point programs by the food industry, the demand for rapid microbial testing has been steadily on the rise (Rules and Regulations, Department of Agriculture Food Safety and Inspection Service, "Pathogen Reduction; Hazard Analysis and Critical Control Point (HACCP) Systems" (1996) 61 Federal Register 38806).

Rapid microbiological methods such as nucleic acid probe hybridization and immunological assays have advanced dramatically, shortening the time required for the detection of pathogens in meats and other foods.

However, these methods require concentrations of target microorganism of $10^4$ to $10^6$ cells per ml or more (Blackburn et al., 1994, Lett. Appl. Microbiol. 19:32–36; Swaminathan et al., 1994, Ann. Rev. Microbiol. 48:401–426; and Tian et al., 1996, J. Food Prot. 59:1158–1163). Foods which are contaminated by bacterial pathogens usually have low numbers of bacteria so that an enrichment step is required prior to the application of a rapid detection assay or even a selective culture method.

PCR-based assays have the potential to overcome the need for long selective enrichment steps due to their ability to detect and identify pathogens in the presence of large numbers of background flora (K. Venkateswaran et al., 1997, Appl. Environ. Microbiol. 63:4127–4131).

Nevertheless, when target pathogen concentrations are low, i.e., less than $10^3$ CFU/g, current PCR procedures require 6 to 18 hours of enrichment prior to PCR amplification in order to detect such target pathogens. This enrichment step not only brings the target pathogen, which may be present at levels of less than 1 cell per ml or gram of food (Swaminathan et al., 1994, Ann. Rev. Microbiol. 48:401426), to PCR detectable levels but also allows for samples to be diluted or filtered to reduce or partially remove PCR inhibitory food components while bringing the target pathogen to a concentration which is detectable (K. Venkateswaran et al., 1997, Appl. Environ. Microbiol. 63:4127–31).

In culture methods, selective reagents are necessary in order to inhibit the growth of competing microorganisms but they also inhibit target bacteria ultimately increasing the time it requires to achieve detectable levels of the target pathogen. Similarly, many foods contain compounds which are inhibitory to the target bacteria and in many cases the target bacterial cells do not revive or revive very slowly. Furthermore, selection media inhibit the "resuscitation" (reviving the viability) of damaged bacteria present, e.g., in meat samples due to freeze thaw cycles, inhibitory food components, or desiccation during processing.

The possibility of selectively concentrating and thereafter recovering and counting or analyzing target bacteria from a food sample, other than by culture methods, while removing background flora and inhibitory compounds would have a tremendous impact on rapid food testing saving time and increasing sensitivities of existing detection techniques.

Zero tolerance standards require the detection of these damaged pathogens even when they are present at minute levels. On the other hand, selective concentration of target bacteria would enable rapid enrichment to be carried out without the addition of selective reagents which are necessary in order to inhibit the growth of background flora but which also inhibit target bacteria and ultimately increase the time it takes to achieve detectable levels of target pathogen. Removal of competing microorganisms and inhibitory compounds found in food samples to affect resuscitation of target pathogens is best accomplished by selective concentration and subsequent wash steps.

In summary, efficient methods for selective affinity concentration and release of a particular pathogen(s) from foods would not only shorten the overall time required for detection of these pathogens, but would allow for more sensitive detection due to more efficient resuscitation of damaged bacteria.

Furthermore, the ability to collect larger more representative samples while selectively concentrating and recovering a specific pathogen from these samples would greatly increase the probability of detecting a pathogen in foods when they are present at extremely low concentrations.

Methods of efficient affinity adsorption and concentration of a microorganism or microorganisms are disclosed in U.S. patent application Ser. No. 09/175,040, filed Oct. 19, 1998, which is incorporated by reference as if fully set forth herein.

This application teaches methods for concentrating a particular microorganism or microorganisms of interest in a sample. The disclosed methods are generally effected by contacting a sample with a cellulosic or chitin matrix to which is bound a cellulose binding protein ("CBP")-receptor (i.e., a first member of a binding pair) or cellulose binding domain ("CBD")-receptor conjugate specific for said microorganism(s).

The methods also include a washing step to remove unbound material of the sample from the matrix. The methods also include an optional step for enriching the concentrated microorganism(s) in situ by addition of a culture medium to the matrix or by enriching the concentrated microorganism(s) in vitro by transferring the microorganism(s) from the matrix to a culture medium. The method also includes an optional step of performing an assay to detect any microorganisms that bind to the CBP- or CBD-receptor conjugate bound to the matrix.

The disclosed methods have utility in concentrating microorganisms in samples, particularly dilute samples, in order to detect the microorganisms by any means known in the art. Such methods of concentration provide improved means of concentrating microorganisms in food, environmental, or biological, such as medical or veterinary, samples.

The disclosed methods have a number of advantages over previously described concentration methods. For example, the use of cellulosic fabric as a matrix allows for larger volumes of liquids (up to 10 liters) to be passed with relatively high flow rates as compared to, for example, the DYNAL® DYNALBEADSO® procedure [Dynal-product Cat. No. 710-03]. The low non-specific binding of the cellulose achieves very low background levels. In certain preferred embodiments, the disclosed methods are able to capture microorganisms present at very low concentrations by use of high surface area cellulosic or chitin matrix, such as, but not limited to gauze. The physical properties of the cellulosic or chitin matrix enable its performance under conditions that Immuno Magnetic Separation (IMS) do not perform effectively, i.e., in the presence of food samples containing milk and food samples containing bacteria at concentrations lower than $10^3$ CFU/ml.

However, no efficient method of releasing the captured microorganism is disclosed in U.S. patent application Ser. No. 09/175,040.

There is also a need for efficient adsorption and release of eukaryotic cells. Of particular interest are bone marrow and hematopoietic derived cells. Particular cell types derived from these sources, such as, but not limited to, hematopoietic stem cells, stromal stem cells, lymphocytes, etc., are used in a variety of therapeutic allogenic and autologous procedures as well as diagnostic procedures. Examples include, but are not limited to, adoptive immunotherapy for treatment of cancers, cartilage damage repair for treatment of damaged joints, gene therapy for treatment of genetic disorders and cancer, analysis of maternal blood derived fetal cells for detection of genetic diseases, removal of cells causing graft vs. host disease in cases of bone marrow transplantation. In most cases, however, the cell types required for such procedures are scarce and need to be separated from a mixed cell population. Affinity adsorption is in many cases employed to separate the required cells from the mixed cell population.

An efficient method of affinity adsorption and concentration of eukaryotic cells is disclosed in PCT/CA97/00033 (WO 97/26358), which is incorporated by reference as if fully set forth herein. This application teaches methods and compositions for isolating growth-factor dependent cells through the use of immobilized growth factors. The compositions include a matrix binding polypeptide and a growth factor conjugate which is used as an affinity complex to adsorb the growth factor dependent cells to the matrix.

Prior art methods of affinity adsorption and release of cells:

The technology for capturing specific cells on affinity matrices is well developed. To this end, see, for example, Wigzel, et al. (1969), J. Exp. Med., 129:23; Schlossman, et al. (1973), J. Immunol., 110:313; Mage, et al. (1977), J. Immunol. Meth., 15:47; Wysocki, et al. (1978), Proc. Nat. Acad. Sci., 75:2844; Schrempf-Decker, et al. (1980), J. Immunol. Meth., 32:285; Muller-Sieburg, et al. (1986), Cell, 44:653, which are incorporated herein by reference.

Various methods have been proposed to effect the release of cells or other target substances from a solid matrix once they have been exclusively adsorbed thereto. U.S. Pat. No. 3,970,518 to Giaever discloses the use of antibody-coated magnetic microspheres to separate cells, and uses a chemical cleaving agent such as formic or sulfuric acids to release the separated cells. U.S. Pat. No. 4,988,621 to Hayman, et al. discloses the use of a short peptide which interferes with the binding of cells to fibronectin, allowing the detachment of cells from a solid matrix. EP 463508 A to Mori discloses the use of a temperature-responsive adhesive to immobilize a cell for microinjection, lowering the temperature to release the immobilized cell. WO 91/16452 to Berenson describes a technique involving agitation of an avidin column to remove cells captured thereon. The use of ionic strength manipulation to reversibly immobilize antibodies bound to magnetic beads has also been reported. See, for example, Scouten, Anal. Biochem. 205:313–18 (1992). U.S. Pat. No. 5,081,030 to Civin discloses the use of chymopapain to digest the cell surface antigen My10, releasing stem cells from magnetic particles used to isolate the stem cells from a cell suspension. WO 94/20858 to Berge et al. describes the separation of target substances by means of a relatively large magnetic particle linked via a hydroxyboryl/cis-diol bond to an antibody, which bond is cleaved after separation of the target substance. The commercially available DETACHaBEAD from Dynal (Oslo, Norway) comprises an anti-mouse FAb with higher affinity for the binding site of a monoclonal antibody than the monoclonal has for its corresponding antigen. Therefore, the anti-FAb antibody can displace the original MAb from a target cell. See Geretti, et al. J. Immunol. Meth. 161:129–31 (1993); and Rasmussen, et al., J. Immunol. Meth. 146:195–202 (1992). WO 94/02016 to Kesler describes the use of an excess of soluble hapten to disrupt a hapten-antihapten complex, thereby releasing a cell from its solid matrix. See also Clark et al., J. Immunol. Meth., 51:167–70 (1982). Competitive affinity elution is disclosed by Grandics, et al. (U.S. Pat. No. 5,773,224).

Some other proposed methods include reduction of disulfides or cleavage of specific linkages by enzymatic or chemical agents inserted somewhere between the capture solid surface and the target cells. Such techniques may include protease digestion of marker antibodies or coupling peptides, cellular oligosaccharides cleavable with glycolytic enzymes, or chemical bonds broken under mild conditions that will preserve biological activity, such as oxidizing, reducing, basic, or acidic conditions. Because of the extreme complexity of cell surfaces and the desire to maintain high cell viability and functional integrity during selection, it is very difficult to find an enzymatic or chemical release method which has no effect on the cell structure and/or function. Mechanical agitation/elution can be damaging to the cell membrane and reduce cell viability.

All of the above methods suffer one or more disadvantages, which may include, low release/elution yields, non-stoichiometric release/elution, low recovery following elution and cell damage. However, all of the above methods share a common limitation—they lack universality.

The following paragraphs provide some more insight into the limitations associated with various prior art approaches of releasing particulates adsorbed to solid matrices.

Thus, a variety of matrices have been employed for capturing specific cells for the isolation thereof from mixed cell populations. In all of these cases the release of the cells involve perturbation of the cell surface or destruction of the immobilizing linker. Each of these treatments can be detrimental to the viability of the recovered cells.

Current methods for releasing cells from surfaces to which they are adsorbed include, for example, chemical treatment, heat treatment, enzymatic treatment, competitive release and release via receptor internalization. Each of these methods suffer limitations as further detailed hereinunder.

Chemical and heat treatments:

Examples for methods which are used to release cells from antibodies bound to a solid matrix include treatment with chaotropic agents, such as, but not limited to, 4.5 M $MgCl_2$ pH 7.5, or 2.5 M NaI pH 7.5 (U.S. Pat. No. 5,415, 997), polarity reducing agents, such as ethylene glycol in solutions of up to 50% (U.S. Pat. No. 5,415,997), and agents that lead to changes in pH, such as glycine/HCl pH 2.5, aqueous $NH_3$ pH 11, and 0.5% KOH pH 12.5 (U.S. Pat. No. 5,415,997), or in ionic strength, such as in the case of oligo dA tagged antibodies which are bound to Dynabeads Oligo-dT. In all of the above cases the viability of the target cells is compromised.

Other methods exist which can be used to release cells which have been captured by different means on a wide variety of solid matrices. High temperatures and other harsh treatments such as lytic reagents (NaOH) and denaturing reagents (5 M urea, 6 M guanidine HCl) can also lead to the release of cells from the matrices to which they are bound, however these cells are not viable. These approaches are suitable if the goal is to perform tests such as DNA analysis or immunoassays for specific antigen of the organisms which are released from the matrix, which can be performed using a non-viable cellular material. However these methods are not suitable for the recovery of viable cells and in some cases the antigen which is the target of an immunoassay may be destroyed by the releasing agent.

It should be noted that even in cases where viable cells are not directly required to perform a test, it may still be desirable to amplify the recovered cells before running the test. This is especially true when the number of cells captured on the matrix is less than the amount required to generate a sufficient signal to give a statistically significant positive result in the test selected.

Elution methods which have a lethal effect on the viability of the targeted cells generates a need for capturing extremely high numbers of target cells in order to recover just a few after elution. Often this demand is answered by prolonged enrichment steps prior to the capture of the target cells. However, these enrichment steps often cause exponential growth of unwanted microorganisms as well, which form a burden to the capture system and its ability to produce isolated target cells following the elution step.

Enzymatic treatment:

In the case of linker-based immobilization through a cell specific antibody or ligand, it is often possible to digest the linker molecule itself. This can be done with general proteases such as proteinase K or pronase, however these enzymes tend to digest proteins nonspecifically, and typically damage cell surface proteins which leads to loss of viability and/or functional activity of the cell surface protein. Even more specific proteases targeted at specific portions of an antibody or ligand often have detrimental affect on cell viability. Furthermore, these specific enzymes are not necessarily very efficient at mediating the quantitative release of cells from the matrix. In general, the efficiency of a particular protease for the release of a cell which has been captured by an antibody or other ligand must be determined empirically. Not every protease performs with every antibody, ligand and/or coupling method. In some cases, the protease concentration required to effect cell release is so high that cell is viability is compromised.

Competitive release:

In some cases, reagents are available which can compete off the bound cells. These may be high concentrations and/or slightly altered soluble forms of the immobilized antibody or ligand. Unfortunately, this approach is often unsuccessful in practice. This may be due, in part, to the fact that the density of the cell surface molecules leads to very high avidity multivalent interactions with the immobilized antibodies or ligands which often require drastic elution conditions which prevent viable cell recovery (Bonnafous J C, et al., J Immunol Methods, 1983 58 (1– 2):93–107). Furthermore, it may be necessary in some cases to produce a competitive reagent specifically for each ligand-target cell pair, rendering this option cost-ineffective and/or impractical. An example of competitive release is shown with the use of methoxyethoxymethyl (MEM) bonded-phase Cellulofine columns to selectively separate human peripheral platelets, granulocytes and lymphocytes. Selective elution was achieved by using different mobile phases containing various saccharides (Shibusawa et al., J. Chromatogr. B. Biomed. Appl. 1995, 666(2):233–239).

Receptor internalization: Release, can in some rare cases, be obtained by simply incubating cells which have been captured over night in cell culture. B cells can be released from Dynabeads after capture by overnight incubation in cell culture which causes transient down regulation of the target surface antigen by the target cell. Again, this method is limited to specific cell types which can and are induced to perform internalization under capture conditions.

There is thus a widely recognized need for, and it would be highly advantageous to have a method of releasing solid matrix affinity adsorbed particulates by enzymatically degrading the solid matrix to which the particulates are adsorbed, because such a method is both universal and it avoids the above limitations associated with prior art release methods.

SUMMARY OF THE INVENTION

It is thus an object of the present invention to provide a method for releasing particulates, such as viruses and cells or portions thereof, either prokaryotic or eukaryotic cells, either cells of microorganisms or cells derived from multicellular organisms, from a solid matrix to which they are adsorbed.

It is another object of the present invention to provide such a method which is universal and is based on degrading the solid matrix via a degrading enzyme.

It is yet another object of the present invention to provide such a method which inflicts substantially no damage upon the particulates.

It is still another object of the present invention to provide such a method which can be used to release close to 100% of the adsorbed particulates in a viable form, even in cases of low cell numbers.

Thus, according to one aspect of the present invention there is provided a method of releasing particulates from a solid matrix, the method comprising the step of adding to the solid matrix a degrading enzyme capable of degrading the solid matrix, to thereby release the particulates from the solid matrix.

According to further features in preferred embodiments of the invention described below, the particulates are adsorbed to the solid matrix.

According to still further features in the described preferred embodiments the particulates are affinity adsorbed to the solid matrix.

According to still further features in the described preferred embodiments the particulates are affinity adsorbed to the solid matrix via an endogenous determinant of the particulates.

According to still further features in the described preferred embodiments the endogenous determinant resides on a surface of the particulate and is selected from the group consisting of a complex carbohydrate, a lipopolysaccharide, a protein and a glycoprotein.

According to still further features in the described preferred embodiments the particulates are affinity adsorbed to the solid matrix via an affinity complex which is bound to the determinant of the particulates on one hand and to the solid matrix on the other hand.

According to still further features in the described preferred embodiments the affinity complex includes at least one affinity moiety selected from the group consisting of an antibody, an antigen, a hapten, a ligand, a soluble receptor, a matrix binding peptide, avidin, streptavidin and biotin.

According to still further features in the described preferred embodiments the ligand is selected from the group consisting of a growth factor, a hormone and a neurotransmitter.

According to still further features in the described preferred embodiments the soluble receptor is selected from the group consisting of a growth factor receptor, a hormone and a neurotransmitter receptor.

According to still further features in the described preferred embodiments the matrix binding peptide is a polysaccharide binding protein.

According to still further features in the described preferred embodiments the matrix binding peptide is a polysaccharide binding domain obtained from a polysaccharidase or from a scaffoldin protein, wherein said peptide essentially lacks hydrolytic activity.

According to still further features in the described preferred embodiments the solid matrix includes a polysaccharide and further wherein the degrading enzyme is a polysaccharidase.

According to still further features in the described preferred embodiments the polysaccharide is selected from the group consisting of a cellulosic material, an agarose, a chitin, a starch and derivatives thereof.

According to still further features in the described preferred embodiments the polysaccharidase is selected from the group consisting of a cellulase, an agarase, a chitinase and an amylase.

According to still further features in the described preferred embodiments the particulates are viruses or portions thereof.

According to still further features in the described preferred embodiments the particulates are microorganisms or portions thereof.

According to still further features in the described preferred embodiments the particulates are cells or portions thereof According to still further features in the described preferred embodiments the cells are selected from the group consisting of prokaryotic cells and eukaryotic cells.

According to still further features in the described preferred embodiments the prokaryotic cells are bacterial pathogens.

According to still further features in the described preferred embodiments the eukaryotic cells are selected from the group consisting of growth factor dependent cells, fetal cells, bone marrow derived cells, blood derived cells and tumor derived cells.

According to still further features in the described preferred embodiments the solid matrix is selected from the group consisting of a fabric, threads, beads (including non-porous beads), a powder, a membrane and a sponge.

According to still further features in the described preferred embodiments the method further comprising the step of eluting the particulates.

According to still further features in the described preferred embodiments the method further comprising the step of recovering the particulates.

According to still further features in the described preferred embodiments the method further comprising the step of separating the particulates and the solid matrix.

According to another aspect of the present invention there is provided a method of releasing growth factor dependent cells from a polysaccharide matrix to which they are adsorbed via an affinity complex including the growth factor and a polysaccharide binding peptide, the method comprising the step of adding to the polysaccharide matrix a polysaccharidase capable of degrading the polysaccharide matrix, to thereby release the growth factor dependent cells from the polysaccharide matrix.

According to yet another aspect of the present invention there is provided a method of releasing a microorganism from a polysaccharide matrix to which they are adsorbed via an affinity complex including a polysaccharide binding peptide-receptor conjugate specific for the microorganism, the method comprising the step of adding to the polysaccharide matrix a polysaccharidase capable of degrading the polysaccharide matrix, to thereby release the microorganism from the polysaccharide matrix.

The present invention successfully addresses the shortcomings of the presently known configurations by providing a universal method of releasing particulates from a solid matrix to which they are adsorbed, which method inflicts substantially no damage upon the released particulates and can be used to release close to 100% of the adsorbed particulates in a viable form, even in cases of low titers.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
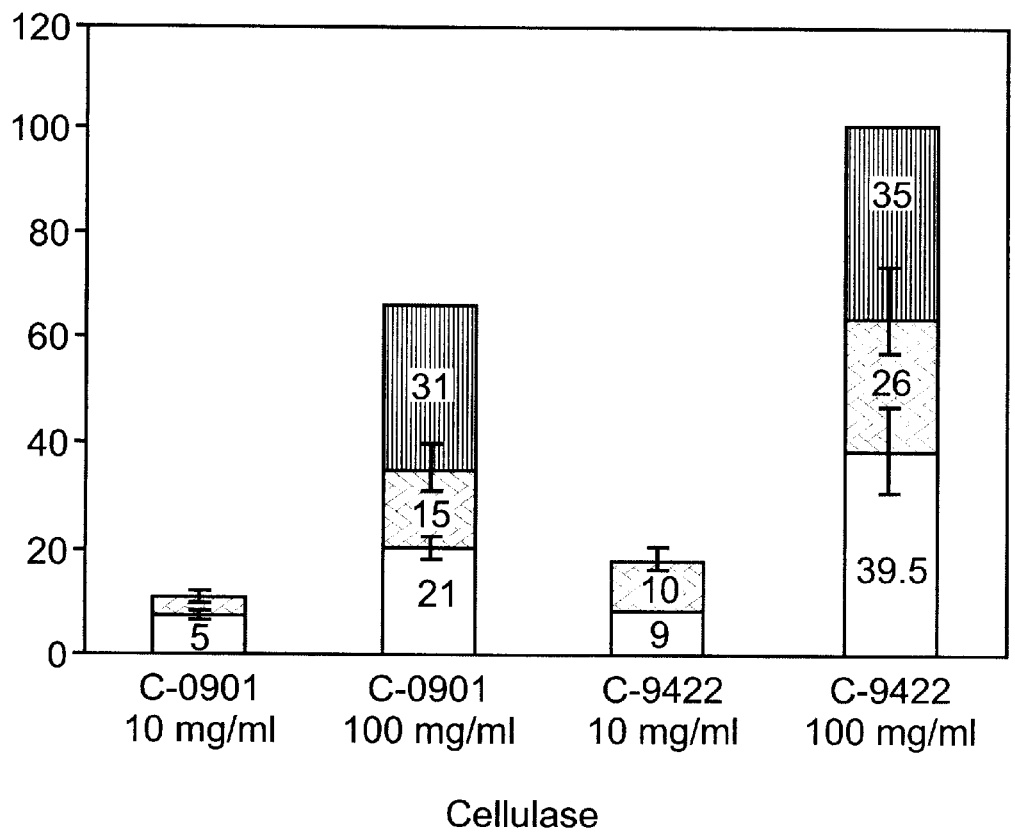
FIG. 1 demonstrates elution of microorganisms which have been captured onto a cellulose solid matrix via a CBD-antibody affinity complex using cellulases. A CBD-IC (immunocolumn) cartridge was used to capture viable *E. coli* O157:H7 from 1 ml PBS solution containing 185 CFU's. After capture and wash steps, each cartridge was incubated for 30 minutes with cellulase to release viable bacteria which were then plated on mENDO LES agar for quantification of CFU's. Lower bar shows bacteria eluted with the original 200 µl cellulase solution, whereas the second bar indicates bacteria that were collected by additional 200 µl of PBS. The third, upper bar, when present, indicates bacteria that were eluted in additional 20 ml of 10 ml PBS-Tween and 10 ml PBS washes. C-9422: *Trichoderma viride* cellulase; C-0901: *Penicillium funiculosum* cellulase.

The present invention is of a method which can be used for releasing solid matrix affinity adsorbed particulates. Specifically, the present invention can be used to release solid matrix affinity adsorbed particulates such as viruses, cells or portions thereof by enzymatically degrading the solid matrix to which the particulates are adsorbed, thereby providing a universal method of releasing particulates from a solid matrix, which method inflicts substantially no damage upon the released particulates and can be used to release close to 100% of the adsorbed particulates in a viable form even when present at ultra low titers.

The principles and operation of a method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Thus, the present invention provides a method of releasing particulates, such as cells or portions thereof, from a solid matrix. The method according to the present invention is effected by adding to the solid matrix a degrading enzyme capable of degrading the solid matrix, to thereby release the particulates from the solid matrix.

As used herein in the specification and in the claims section below, the verb "to release" includes to free, to dissociate and/or to detach.

The particulates according to the present invention can be adsorbed to the solid matrix. They can be either affinity adsorbed or non-specifically adsorbed to the solid matrix. By "affinity adsorbed" it is meant that the particulates are directly or indirectly bound to the solid matrix via an affinity complex at affinity sites. By "non-specifically adsorbed" it is meant that the particulates are bound to the solid matrix via non-specific interactions which are known to be weaker.

In both cases, the interactions between an endogenous determinant (which forms a first member of a binding pair) present on the surface of the particulate as further detailed below, and the affinity complex (which forms a second member of the binding pair)—for affinity adsorption; or between various (non-specific) determinants of the particulate and the solid matrix—for non-specific adsorption, are typically effected through non-covalent interactions, such as, for example, electrostatic, polar, hydrophobic and/or Van der Waals interactions. The interactions between the affinity complex and the solid matrix can be either affinity non-covalent interactions as described above, or alternatively, covalent interactions.

The particulates can be affinity adsorbed to the solid matrix via an endogenous determinant of the particulates. Such a determinant can be, for example, a determinant that resides on a surface of the particulate. Such a determinant can include, for example, a complex carbohydrate, a lipopolysaccharide, a protein and/or a glycoprotein.

Some complex carbohydrates (e.g., sialyl-Lewis$^x$ (SLe$^x$) and other carbohydrate moieties involved in cell adhesion and signaling), proteins, glycoproteins and lipopolysaccharides form endogenous surface determinants which are well known to be specific to different types of cells.

For example, different cells of the hematopoietic lineage include unique determinants which are frequently used to identify and isolate such cells from a mixed cell population. These include, for example, the CD4 and CD8 antigen determinants of hematopoietic cells. Additional examples include MHC antigens and receptors. Other examples include growth factor receptors, e.g., steel factor receptor, epidermal growth factor receptor, nerve growth factor receptor, brain derived neurotrophic factor receptor, erythropoietin receptor, GM-CSF receptor; interleukin (including IL-2 and IL-3 and others) receptor, platelet derived growth factor receptor (PDGFR), and the like. Still additional examples include hormone receptors, e.g., insulin receptor, glucagon receptor and the like. Other examples include receptors for neurotransmitters. Yet other examples include cell adhesion receptors/cell scaffold determinants, such as, but not limited to, integrins, LAM-1, ICAM-1, LFA-3, H-CAM, ELAM-1. Still additional examples include cell transporters, such as antiporters, coporters and ATP dependent transporters.

Also bacterial species and strains differ from one another by endogenous determinants thereof, e.g., in their lipopolysaccharides and/or flagellar proteins. This is specifically characteristic of pathogenic versus non-pathogenic strains of a single bacterial species, wherein determinants which are unique to the pathogenic strain are related to the pathogeneity thereof and are absent in the non-pathogenic strain.

Indeed, through the years of biological and medical research a variety of cell specific determinants have been characterized for a variety of both eukaryotic and prokaryotic cells. These determinants, such as receptors, selecting, cell scaffolds proteins, and the like surface determinants, which serve any one of a plurality of biological functions, can be used for affinity adsorption of specific cell types as further detailed hereinunder.

According to a preferred embodiment of the present invention the particulates are affinity adsorbed to the solid matrix via an affinity complex which is bound to the endogenous surface determinant of the particulates on one hand, and to the solid matrix on the other hand.

The affinity complex which is used according to the present invention to affinity adsorb the particulates to the solid matrix can include one or more affinity moieties (which, for example, form the second member of the binding pair), such as, but not limited to, an antibody, an antigen, a hapten, a ligand, a soluble receptor, a matrix binding peptide, avidin, streptavidin and biotin.

As used herein in the specification and in the claims section below, the term "antibody" include serum immunoglobulins, polyclonal antibodies or fragments thereof or monoclonal antibodies or fragments thereof. The antibodies are preferably elicited against a surface determinant of the particulate. Monoclonal antibodies or purified fragments of the monoclonal antibodies having at least a portion of an antigen binding region, including such as Fv, F(abl)2, Fab fragments (Harlow and Lane, 1988 Antibody, Cold Spring Harbor), single chain antibodies (U.S. Pat. No. 4,946,778), chimeric or humanized antibodies (Morrison et al., 1984, Proc. Natl. Acad. Sci. USA 81:6851; Neuberger et al., 1984, Nature 312:604–8) and complementarily determining regions (CDR) may be prepared by conventional procedure. Purification of the serum immunoglobulins antibodies or fragments can be accomplished by a variety of methods known to those of skill including, but not limited to, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104–126, 1986, Orlando, Fla., Academic Press).

As used herein in the specification and in the claims section below, the terms "antigen" and "thaptent" include moieties which are specifically recognized by either antibodies as defined above and/or receptors of immune system cells.

As used herein in the specification and in the claims section below, the term "aligand" includes moieties capable of specifically binding to a receptor. Examples of ligands which can be used in an affinity complex according to the present invention include, but are not limited to, growth factors, hormones and neurotransmitters.

As used herein in the specification and in the claims section below, the term "[1]a soluble receptor" includes soluble extracellular portions of cellular receptors which retain their ligand binding activity. These may include soluble portions of growth factor, hormone and neurotransmitter receptor s.

As used herein in the specification and in the claims section below, the term "a matrix binding peptide" include peptides e.g., proteins and domains thereof, which are capable of binding to the solid matrix.

Such peptides include amino acid sequences that are derived from a matrix binding region, of e.g., a polysaccharide binding protein or a polysaccharide binding domain of a polysaccharidase. The polysaccharide binding peptide can include any amino acid sequence or a glycoprotein derivative thereof which binds to an oligosaccharide polymer, for example, the polysaccharide binding domain or protein can be derived from a polysaccharidase, a binding domain of a polysaccharide binding protein or a protein designed and engineered to be capable of binding to a polysaccharide. The polysaccharide binding domain or protein can be naturally occurring or synthetic. Suitable polysaccharidases from which a polysaccharide binding domain or protein may be obtained include β-14-glucanases. In a preferred embodiment, a polysaccharide binding domain or protein from a cellulase is used. Typically, the amino acid sequence is essentially lacking in the hydrolytic activity of the polysaccharidase, but retains the substrate binding activity. The amino acid sequence preferably has less than about 10% of the hydrolytic activity of the native polysaccharidase; more preferably less than about 5%, and most preferably less than about 1% of the hydrolytic activity of the native polysaccharidase, ideally no activity altogether.

The polysaccharide binding domain or protein can be obtained from a variety of sources, including enzymes and other proteins which bind to polysaccharides which find use in the subject invention. In Table 5 below are listed those binding domains which bind to one or more soluble/insoluble polysaccharides including all binding domains with affinity for soluble glucans (α, β, and/or mixed linkages). The N1 cellulose-binding domain from endoglucanase CenC of C. fimi is the only protein known to bind soluble cellosaccharides and one of a small set of proteins which are known to bind any soluble polysaccharides. Also, listed in Tables 1 to 4 are examples of proteins containing putative β-1,3-glucan-binding domains (Table 1); proteins containing Streptococcal glucan-binding repeats (Cpl superfamily) (Table 2); enzymes with chitin-binding domains (Table 3), and starch-binding domains (Table 4). Scaffoldin proteins which include a cellulose binding domain protein such as that produced by Clostridium cellulovorans (Shoseyov et al., PCT/US94/04132) can also be used for preparing a polysaccharide binding domain or protein. Several fungi, including Trichoderma species and others, also produce polysaccharidases from which polysaccharide binding domains or proteins can be isolated. Additional examples can be found in, for example, Microbial Hydrolysis of Polysaccharides, R. A. J. Warren, Annu. Rev. Microbiol. 1996, 50:183–212; and "Advances in Microbial Physiology" R. K. Poole, Ed., 1995, Academic Press Limited, both are incorporated by reference as if fully set forth herein. In addition, U.S. Pat. No. 5,643,758 teaches a maltose binding protein capable of binding to the polysaccharide α-amylose.

TABLE 1

Overview of proteins containing putative β-1,3 glucan-binding domains

| Source (strains) | Protein | accession No. | Ref[1] |
|---|---|---|---|
| Type I | | | |
| B. circulans (WL-12) | GLCA1 | P23903/M34502/JQ0420 | 1 |
| B. circulans (IAM 1165) | BglH | JN0772/D17519/S67033 | 2 |
| Type II | | | |
| Actinomadua sp. (FC7) | XynII | U08894 | 3 |
| Arthrobacter sp. (YCWD3) | GLCI | D23668 | 9 |
| O. xanthineolytica | GLC | P22222/M60826/A39094 | 4 |
| R. faecitabidus (YLM-50 | RP I | Q05308/A45053/D10753 | 5a, b |
| R. communis | Ricin | A12892 | 6 |
| S. lividans (1326) | XlnA | P26514/M64551/JS07986 | 7 |
| T. tridentatus | FactorGa | D16622 | 8 |

B.: Bacillus, O.: Oerskovia, R. faecitabidus: Rarobacter faecitabidus, R. communis: Ricnius communis, S.: Streptomyces, T.: Tachypleus (Horseshoe Crab)
[1]References:
1) Yahata et al. (1990) Gene 86, 113–117
2) Yamamoto et al. (1993) Biosci. Biotechnol. Biochem. 57, 1518–1525
3) Harpin et al. (1994) EMBL Data Library
4) Shen et al. (1991) J. Biol. Chem. 266, 1058–1063
5a) Shimoi et al. (1992) J. Biol. Chem. 267, 25189–25195
5b) Shimoi et al. (1992) J. Biochem 110, 608–613
6) Horn et al. (1989) Patent A12892
7) Shareck et al. (1991) Gene 107, 75–82
8) Seki et al. (1994) J. Biol. Chem. 269, 1370–1374
9) Watanabe et al. (1993) EMBL Data Library

TABLE 2

Overview of proteins containing Streptococcal glucan-binding repeats (Cpl superfamily)

| Source | Protein | Accession No. | Ref.[2] |
|---|---|---|---|
| S. downei (sobrinus) (OMZ176) | GTF-I | D13858 | 1 |
| S. downei (sobrinus) (MFe28) | GTF-I | P11001/M17391 | 2 |
| S. downei (sobrinus) (MFe28) | GTF-S | P29336/M30943/A41483 | 3 |
| S. downei (sobrinus) (6715) | GTF-I | P27470/D90216/A38175 | 4 |

TABLE 2-continued

Overview of proteins containing *Streptococcal glucan*-binding repeats (Cpl superfamily)

| Source | Protein | Accession No. | Ref.[2] |
|---|---|---|---|
| S. downei (sobrinus) | DEI | L34406 | 5 |
| S. mutants (Ingbritt) | GBP | M30945/A37184 | 6 |
| S. mutants (GS-5) | GTF-B | A33128 | 7 |
| S. mutants (GS-5) | GTF-B | P08987/M17361/B33135 | 8 |
| S. mutants | GTF[3'-ORF] | P05427/C33135 | 8 |
| S. mutants (GS-5) | GTF-C | P13470/M17361/M22054 | 9 |
| S. mutants (GS-5) | GTF-C | not available | 10 |
| S. mutants (GS-5) | GTF-D | M29296/A45866 | 11 |
| S. salivarius | GTF-J | A44811/S22726/S28809 Z11873/M64111 | 12 |
| S. salivarius | GTF-K | S22737/S22727/Z11872 | 13 |
| S. salivarius (ATCC25975) | GTF-L | L35495 | 14 |
| S. salivarius (ATCC25975) | GTF-M | L35928 | 14 |
| S. pneumoniae R6 | LytA | P06653/A25634/M13812 | 15 |
| S. pneumoniae | PspA | A41971/M74122 | 16 |
| Phage HB-3 | HBL | P32762/M34652 | 17 |
| Phage Cp-1 | CPL-1 | P15057/J03586/A31086 | 18 |
| Phage Cp-9 | CPL-9 | P19386/M34780/JQ0438 | 19 |
| Phage EJ-1 | EJL | A42936 | 20 |
| C. difficile (VPI 10463) | ToxA | P16154/A37052/M30307 X51797/S08638 | 21 |
| C. difficile (BARTS W1) | ToxA | A60991/X17194 | 22 |
| C. difficile (VPI 10463) | ToxB | P18177/X53138/X60984 S10317 | 23, 24 |
| C. difficile (1470) | ToxB | S44271/Z23277 | 25, 26 |
| C. novyi | a-toxin | S44272/Z23280 | 27 |
| C. novyi | a-toxin | Z48636 | 28 |
| C. acetobutylicum (NCIB8052) | CspA | S49255/Z37723 | 29 |
| C. acetobutylicum (NCIB8052) | CspB | Z50008 | 30 |
| C. acetobutylicum (NCIB8052) | CspC | Z50033 | 30 |
| C. acetobutylicum (NCIB8052) | CspD | Z50009 | 30 |

[2]References:
1) Sato et al. (1993) DNA sequence 4, 19–27
2) Ferreti et al. (1987) J. Bacteriol. 169, 4271–4278
3) Gilmore et al. (1990) J. Infect. Immun. 58, 2452–2458
4) Abo et al. (1991) J. Bacteriol. 173, 989–996
5) Sun et al. (1994) J. Bacteriol. 176, 7213–7222
6) Banas et al. (1990) J. Infect. Immun. 58, 667–673
7) Shiroza et al. (1990) Protein Sequence Database
8) Shiroza et al. (1987) J. Bacteriol. 169, 4263–4270
9) Ueda et al. (1988) Gene 69, 101–109
10) Russel (1990) Arch. Oral. Biol. 35, 53–58
11) Honda et al. (1990) J. Gen. Microbiol. 136, 2099–2105
12) Giffard et al. (1991) J. Gen. Microbiol. 137, 2577–2593
13) Jacques (1992) EMBL Data Library
14) Simpson et al. (1995) J. Infect. Immun. 63, 609–621
15) Gargia et al. (1986) Gene 43, 265–272
16) Yother et al. (1992) J. Bacteriol. 174, 601–609
17) Romero et al. (1990) J. Bacteriol. 172, 5064–5070
18) Garcia et al. (1988) Proc. Natl. Acad. Sci, USA 85, 914–918
19) Garcia et al. (1990) Gene 86, 81–88
20) Diaz et al. (1992) J. Bacteriol. 174, 5516–5525
21) Dove et al. (1990) J. Infect. Immun. 58, 480–488
22) Wren et al. (1990) FEMS Microbiol. Lett. 70, 1–6
23) Barroso et a. (1990) Nucleic Acids Res. 18, 4004–4004
24) von Eichel-Streiber et al. (1992) Mol. Gen. Genet. 233, 260–268
25) Sartinger et al. (1993) EMBL Data Library
26) von Eichel-Streiber et al. (1995) Mol. Microbiol. In Press
27) Hofmann et al. (1993) EMBL Data Library
28) Hofmann et al. (1995) Mol. Gen. Genet. In Press
29) Sanchez et al. (1994) EMBL Data Library
30) Sanchez et al. (1995) EMBL Data Library New polysaccharide binding domains or proteins with interesting binding characteristics and specificities can be identified and screened for in a variety of ways including spectroscopic (titration) methods such as: NMR spectroscopy (Zhu et al. Biochemistry (1995) 34:13196–13202, Gehring et al. Biochemistry (1991) 30:5524–5531), UV difference spectroscopy (Belshaw et al. Eur. J. Biochem. (1993) 211:717–724), fluorescence (titration) spectroscopy (Miller et al. J. Biol. Chem. (1983) 258:13665–13672), UV or fluorescence stopped flow analysis (De Boeck et al. Eur. J. Biochem. (1985) 149:141–415), affinity methods such as affinity electrophoresis (Mimura et al. J. chromatography (1992) 597:345–350) or affinity chromatography on immobilized mono or oligosaccharides, precipitation or agglutination analysis including turbidimetric or nephelometric analysis (Knibbs et al. J. Biol. Chem. (1993) 14940–14947), competitive inhibition assays (with or without quantitative IC50 determination) and various physical or physicochemical methods including differential scanning or isothermal titration calorimetry (Sigurskjold et al. J. Biol. Chem. (1992) 267:8371–8376; Sigurskjold et al. Eur. J. Biol. (1994) 225:133–141) or comparative protein stability assays (melts) in the absence or presence of oligo saccharides using thermal CD or fluorescence spectroscopy.

The $K_a$ for binding of the polysaccharide binding domains or proteins to oligosaccharide is at least in the range of weak antibody-antigen extractions, i.e., $\geq 10^3$, preferably $10^4$, most preferably $10^6$ M$^{-1}$. If the binding of the polysaccharide binding domain or protein to the oligosaccharide is exothermic or endothermic, then binding will increase or decrease, respectively, at lower temperatures, providing a means for temperature modulation of the immobilization step.

TABLE 3

Overview of enzymes with chitin-binding domains

| Source (strain) | Enzyme | Accession No. | Ref.[3] |
|---|---|---|---|
| Bacterial enzymes | | | |
| Type I | | | |
| Aeromonas sp. (No10S-24) | Chi | D31818 | 1 |
| Bacillus circulans (WL-12) | ChiA1 | P20533/M57601/A38368 | 2 |
| Bacillus circulans (WL-12) | ChiD | P27050/D10594 | 3 |
| Janthinobacterium lividum | Chi69 | U07025 | 4 |
| Streptomyces griseus | ProteaseC | A53669 | 5 |

TABLE 3-continued

Overview of enzymes with chitin-binding domains

| Source (strain) | Enzyme | Accession No. | Ref.[3] |
|---|---|---|---|
| *Type II* | | | |
| *Aeromonas cavia* (K1) | Chi | U09139 | 6 |
| *Alteromonas sp* (0–7) | Chi85 | A40633/P32823/D13762 | 7 |
| *Autographa californica* (C6) | NPH-128[a] | P41684/L22858 | 8 |
| *Serratia marcescens* | ChiA | A25090/X03657/L01455/P07254 | 9 |
| *Type III* | | | |
| *Rhizopus oligosporus* (1F08631) | Chi1 | P29026/A47022/D10157/527418 | 10 |
| *Rhizopus oligosporus* (1F08631) | Chi2 | P29027/B47022/D10158/S27419 | 10 |
| *Saccharoinyces cerevisiae* | Chi | S50371/U17243 | 11 |
| *Saccharomyces cerevisiae* (DBY939) | Chi 1 | P29028/M74069 | 12 |
| *Saccharomyces cerevisiae* (DBY918) | Chi2 | P29029/M7407/B41035 | 12 |
| Plant enzymes | | | |
| Hevein superfamily | | | |
| *Allium sativum* | Chi | M94105 | 13 |
| *Amaranthus caudatus* | AMP-1[b] | P27275/A40240 | 14, 15 |
| *Amaranthus caudatus* | AMP-2[b] | S37381/A40240 | 14, 15 |
| *Arabidopsis thaliana* (cv. colombia) | ChiB | P19171/M38240/B45511 | 16 |
| *Arabidopsis thaliana* | PHP[c] | U01880 | 17 |
| *Brassica napus* | Chi | U21848 | 18 |
| *Brassica napus* | Chi2 | Q09023/M95835 | 19 |
| *Hevea brasiliensis* | Hev1[d] | P02877/M36986/A03770/A38288 | 20, 21 |
| *Hordeum vulgare* | Chi33 | L34211 | 22 |
| *Lycopersicon esculentum* | Chi9 | Q05538/Z15140/S37344 | 23 |
| *Nicotiana tabacum* | CBP20[e] | S72424 | 24 |
| *Nicotiana tabacum* | Chi | A21091 | 25 |
| *Nicotiana tabacum* (cv. Havana) | Chi | A29074/M15173/S20981/S19855 | 26 |
| *Nicotiana tabacum* (FB7-1) | Chi | JQ0993/S0828 | 27 |
| *Nicotiana tabacum* (cv. Samsun) | Chi | A16119 | 28 |
| *Nicotiana tabacum* (cv. Havana) | Chi | P08252/X16939/S08627 | 27 |
| *Nicotiana tabacum* (cv. BY4) | Chi | P24091/X51599/X64519//S13322 | 26, 27, 29 |
| *Nicotiana tabacum* (cv. Havana) | Chi | P29059/X64518/S20982 | 26 |
| *Oryza sativum* (1R36) | ChiA | L37289 | 30 |
| *Oryza sativum* | ChiB | JC2253/S42829/Z29962 | 31 |
| *Oryza sativum* | Chi | 539979/S40414/X56787 | 32 |
| *Oryza sativum* (cv. Japonicum) | Chi | X56063 | 33 |
| *Oryza sativum* (cv. Japonicum) | Chi1 | P24626/X54367/S14948 | 34 |
| *Oryza sativum* | Chi2 | P25765/S15997 | 35 |
| *Oryza sativum* (cv. Japonicum) | Chi3 | D16223 | |
| *Oryza sativum* | ChiA | JC2252/542828 | 30 |
| *Oryza sativum* | Chi1 | D16221 | 32 |
| *Oryza sativum* (1R58) | Chi | U02286 | 36 |
| *Oryza sativum* | Chi | X87109 | 37 |
| *Pisum sativum* (cv. Birte) | Chi | P36907/X63899 | 38 |
| *Pisum sativum* (cv. Alcan) | Chi2 | L37876 | 39 |
| *Populus trichocaipa* | Chi | S18750/S18751/X59995P29032 | 40 |
| *Populus trichocarpa* (H11-11) | Chi | U01660 | 41 |
| *Phaseolus vulgaris* (cv. Saxa) | Chi | A24215/S43926/Jq0965/P36361 | 42 |
| *Phaseolus vulgaris* (cv. Saxa) | Chi | P06215/M13968/M19052/A25898 | 43, 44, 45 |
| *Sambucus nigra* | PR-3[f] | Z46948 | 46 |
| *Secale cereale* | Chi | JC2071 | 47 |
| *Solanum tuberosum* | ChiB1 | U02605 | 48 |
| *Soianum tuberosum* | ChiB2 | U02606 | 48 |
| *Solanum tuberosum* | ChiB3 | U02607/S43317 | 48 |
| *Solanum tuberosum* | ChiB4 | U02608 | 48 |
| *Solanum tuberosum* (cv. Maris Piper) | WIN-1[g] | P09761/X13497/S04926 | 49 |
| *Solanum tuberosum* (cv. Maris Piper) | WIN-2[g] | P09762/X13497/S04927 | 49 |
| *Triticum aestivum* | Chi h | S38670/X76041 | 50 |
| *Triticum aestivum* | WGA-1[h] | P10968/M25536/S09623/S07289 | 51, 52 |
| *Triticum aestivum* | WGA-2[h] | P02876/M25537/S09624 | 51, 53 |
| *Triticum aestivum* | WGA-3 | P10969/J02961/S10045/A28401 | 54 |
| *Ulmus americana* (NPS3-487) | Chi i | L22032 | 55 |
| *Urtica dioica* | AGL | M87302 | 56 |
| *Vigna unguicuiata* (cv. Red caloona) | Chi1 | X88800 | 57 |

[a]NHP: nuclear polyhedrosis virus endochitinase like sequence; Chi: chitinase,

TABLE 3-continued

Overview of enzymes with chitin-binding domains

Source (strain)　　　　　　　　Enzyme　Accession No.　　　　　　Ref.[3]

[b]anti-microbial peptide,
[c]pre-hevein like protein,
[d]hevein,
[e]chitin-binding protein,
[f]pathogenesis related protein,
[g]wound-induced protein,
[h]wheat germ agglutinin,
[i]agglutinin (lectin).
[3]References:
1) Udea et al. (1994) J. Fennent. Bioeng. 78, 205–211
2) Watanabe et al. (1990) J. Biol. Chem. 265, 15659–16565
3) Watanabe et al. (1992) J. Bacteriol. 174, 408–414
4) Gleave et al. (1994) EMBL Data Library
5) Sidhu et al. (1994) J. Biol. Chem. 269, 20167–20171
6) Jones et al. (1986) EMBO J. 5, 467–473
7) Sitrit et al. (1994) EMBL Data Library
8) Genbank entry only
9) Tsujibo et al. (1993) J. Bacteriol. 175, 176–181
10) Yanai et al. (1992) J. Bacteriol. 174, 7398–7406
11) Panley (1994) EMBL Data Library
12) Kuranda et al. (1991) J. Biol. Chem. 266, 19758–19767
13) van Danime et al. (1992) EMBL Data Library
14) Broekaert et al. (1992) Biochemistry 31, 4308–4314
15) de Bolle et al. (1993) Plant Mol. Physiol. 22, 1187–1190
16) Samac et al. (1990) Plant Physiol. 93, 907–914
17) Potter et al. (1993) Mol. Plant Microbe Interact. 6, 680–685
18) Buchanan-Wollaston (1995) EMBL Data Library
19) Hamel et al. (1993) Plant Physiol. 101, 1403–1403
20) Broekaert et al. (1990) Proc. Natl. Acad. Sci. USA 87, 7633–7637
21) Lee et al. (1991) J. Biol. Chem. 266, 15944–15948
22) Leah et al. (1994) Plant Physiol. 6, 579–589
23) Danhash et al. (1993) Plant Mol. Biol. 22 1017–1029
24) Ponstein et al. (1994) Plant Physiol. 104, 109–118
25) Meins et al. (1991) Patent EP0418695-A1
26) van Buuren et al. (1992) Mol. Gen. Genet. 232, 460–469
27) Shinshi et al. (1990) Plant Mol. Biol. 14, 357–368
28) Cornellisen et al. (1991) Patent EP0440304-A2
29) Fukuda et al. (1991) Plant Mol. Biol. 16, 1–10
30) Yun et al. (1994) EMBL Data Library
31) Kim et al. (1994) Biosci. Biotechnol. Biochem. 58, 1164–1166
32) Nishizawa et al. (1993) Mol. Gen. Genet. 241, 1–10
33) Nishizawa et al. (1991) Plant Sci 76, 211–218
34) Huang et al. (1991) Plant Mol. Biol. 16, 479–480
35) Zhu et al. (1991) Mol. Gen. Genet. 226, 289–296
36) Muthukrishhnan et al. (1993) EMBL Data Library
37) Xu (1995) EMBL Data Library
38) Vad et al. (1993) Plant Sci 92, 69–79
39) Chang et al. (1994) EMBL Data Library
40) Davis et al. (1991) Plant Mol. Biol. 17, 631–639
41) Clarke et al. (1994) Plant Mol. Biol. 25, 799–815
42) Broglie et al. (1989) Plant Cell 1, 599–607
43) Broglie et al. (1986) Proc. Natl. acad. Sci. USA 83, 6820–6824
44) Lucas et al. (1985) FEBS Lett. 193, 208–210
45) Hedrick et al. (1988) Plant Physiol. 86, 182–186
46) Roberts et al. (1994) EMBL Data LibraryI
47) Vamagami et al. (1994) Biosci. Biotechnol. Biochem. 58, 322–329
48) Beerhues et al. (1994) Plant Mol. Biol. 24, 353–367
49) Stanford et al. (1989) Mol. Gen. Genet. 215, 200–208
50) Liao et al. (1993) EMBL Data Library
51) Smith et al. (1989) Plant Mol. Biol. 13, 601–603
52) Wright et al. (1989) J. Mol. Evol. 28, 327–336
53) Wright et al. (1984) Biochemistry 23, 280–287
54) Raikhel et al. (1987) Proc. Natl. acad. Sci. USA 84, 6745–6749
55) Hajela et al. (1993) EMBL Data Library
56) Lerner et al. (1992) J. Biol. Chem. 267, 11085–11091
57) Vo et al. (1995) EMBL Data Library

TABLE 4

Overview of enzymes containing starch-binding domains

| Source (strain) | Enzyme | Accession No. | Ref.[4] |
|---|---|---|---|
| A. awarori (var. kawachi) | AMYG | P23176/D00427/JT0479 | 1, 2 |
| A. niger (T21) | AMYG | S73370 | 3 |
| A. niger -A. awamori | AMYG1/G2 | P04064/A90986/A29166/X00712/X00548 K02465 | 4, 5, 6 7, 8, 9 |
| A. oryzae | AMYG (GLAA) | P36914/JQ1346/D01035/S75274/ D01108 | 10, 11 |
| A. Shirousamii | AMYG (GLA) | P22832/JQ0607/D10460 | 12 |
| Bacillus sp. (B1018) | AMY[a] | P17692/M33302/D90112/S09196 | 13 |
| Bacillus sp. (TS-23) | a-AMY | U22045 | 14 |
| Bacillus sp. (1-1) | CGT | P31746/526399 | 15 |
| Bacillus sp. (6.63) | CGT | P31747/X66106/S21532 | 16 |
| Bacillus sp. (17-1) | CGT | P30921/M28053/A37208 | 17 |
| Bacillus sp. (38-2) | CGT | P09121/M19880/D00129/S24193 | 18, 19 |
| Bacillus sp. (1011) | CGT | P05618/A26678/M17366 | 20 |
| Bacillus sp. (DSM5850) | CGT | A18991 | 21 |
| Bacillus sp. (KC 201) | CGT | D13068 | 15, 22 |
| B. cereus (SPOII) | b-AMY | A48961/P36924/554911 | 23 |
| B. circulans (8) | CGT | P30920/X68326/S23674 | 24 |
| B. circulans (251) | CGT | X78145 | 25 |
| B. Licheniformis | CGTA | P14014/X15752/S15920 | 26 |
| B. macerans (IFO 3490) | CGTM (CDG1) | P04830/X5904/S31281 | 27 |
| B. macerans (IAM 1243) | CGT | M12777 | 28 |
| B. macerans | CGT (CDG2) | P31835/S26589 | 29 |
| B. ohbensis | CGT | P27036/D90243 | 30 |
| B. stearothermophilus | AMYM[b] | P19531/M36539/S28784 | 31 |
| B. stearothermophilus (NO2) | CGT | P31797/X59042/S26588/X59043/ X59404/S31284 | 32 |
| C. rolfsii (AHU 9627) | AMYG2 | D49448 | 33 |
| D. discoideum | ORF | S15693/X51947 | 34 |
| H. grisea (var. themoidea) | GLA1 | M89475 | 35 |
| H. resinae (ATCC20495) | GAMP | Q03045/X68143/X67708/S31422/ S33908 | 36–38 |
| K. pneumoniae (M5A1) | CGT | P08704/M15264/A29023 | 39 |
| N. crassa (74-OR23-1A) | GLA-1 | P14804/X67291/S13711/S13710/ S36364 | 40, 41 |
| P. saccharophila (IAM 1504) | MTA[c] | P22963/X16732/S05667 | 42 |
| Pseudomonas sp. (KO-8940) | AMF-1[d] | D10769/JS0631/D01143 | 43 |
| P. stutzeri (MO-19) | AMYP[c] | P13507/M24516/A32803 | 44 |
| S. griseus (IMRU 3570) | AMY | P30270/X57568/S14063 | 45 |
| S. limosus (S. albidoflavus) | AML | P09794/M18244/B28391 | 46 |
| S. violaceus (S. venezuela) (ATCC15O68) | AML | P22998/M25263/JS0101 | 47 |
| Th. curvata (CCM 3352) | TAM[e] | P29750/X59159/JH0638 | 48 |
| Th. thermosulfurogenes[f] (DSM3896/EM1) | AMYA | P26827/X54654/X54982/ S17298/S37706 | 49 |
| Th. Thermosulfurogenes (ATCC 33743) | AMYB | P19584/M22471/A31389 | 50 |

[a]Raw-starch digesting amylase,
[b]Maltogenic α-amylase,
[c]Maltotetraose-forming amylase (1,4-α-maltotetrahydrolase),
[d]Maltopentaose-forming amylase,
[e]thermostable α-amylase,
[f]formerly *Clostridium thermosulfurogenes*
AMYG, GAM and GLA: glucoamylase, AMY or AML: alpha-amylase, CGT: β-cyclodextrin glycosyltransferase or cyclomaltodextrin glucanotransferase, ORF: open reading frame. A.: Aspergillus, B.: Bacillus, C.: Corticium, D.: Dictiostelium, *H. grisea: Humicola grisea, H. resinea: Hormoconis resinae (Amorphotheca resinae)*, K.: Klebsiella, N.: Neurospora, S.: Streptomyces, *Th. curvata: Thermomonospora curvata*, Th.: Thermoanaerobacter.
[4]References:
1) Hayashida et al. (1989) Agric. Biol. Chem. 53, 135–141
2) Hayashida et al. (1989) Agric. Biol. Chem. 53, 923–929
3) Zhong et al. (1994) Wei Sheng Wu Hseuh Pao 34, 184–190
4) Boel et al. (1984) EMBO J. 3, 1097–1102
5) Boel et al. (1984) EMBO J. 3, 1581–1583
6) Svensson et al. (1986) Eur. J. Biochem. 154, 497–502
7) Svensson et al. (1983) Carlsberg Res. Commun.. 48, 529–544
8) Nunberg et al. (1984) Mol. Cell. Biol. 4, 2306–2315
9) Flwer et al. (1990) Curr. Genet. 18, 537–545
10) Hata et al. (1991) Agric. biol. Chem. 55, 941–949
11) Hata et al. (1991) Gene 108, 145–150
12) Shibuya et al. (1990) Agric. Biol. Chem. 54, 1905–1914
13) Itkor et al. (1990) Biochem. Biophys. res. Commun. 166, 630–636
14) Lin et al. (1995) EMBL Data Library

TABLE 4-continued

Overview of enzymes containing starch-binding domains

| Source (strain) | Enzyme | Accession No. | Ref.[4] |
|---|---|---|---|

15) Schimd et al. (1988) Proceedings of the fourth International symposium on cyclodextrins. Huber, O. and Szejtli, J. Eds. pp 71–76. Kluwer, Academic Publishers.
16) Akhmetzjanov (1992) EMBL Data Library
17) Kaneko et al. (1989) J. Gen. Microbiol. 135, 3447–3457
18) Kaneko et al. (1988) J. Gen. Microbiol. 134, 97–105
19) Hamamoto et al. (1987) Agric. Biol. Chem. 51, 2019–2022
20) Kimura et al. (1987) J. Bacteriol. 169, 4399–4402
21) Patent W09114770-A1
22) Kitamoto et al. (1992) J. Ferment. Bioeng. 74, 345–351
23) Nanmori et al. (1993) Appl. Environ. Microbiol. 59, 623–627
24) Nitschke et al. (1990) Appl. Microbiol. Biotechnol. 33, 542–546
25) Lawson et al. (1994) J. Mol. Biol. 236, 590–560
26) Hill et al. (1990) Nucleids Acids Res. 18, 199–199
27) Fujiwara et al. (1992) Appl. Environ. Microbiol. 58, 4016–4025
28) Takano et al. (1986) J. Bacteriol. 166, 1118–1122
29) Sugimoto et al. Patent N UK2169902
30) Sin et al. (1991) Appl. Microbiol. Biotechnol. 35, 600–605
31) Didericksen et al. (1988) FEMS Microbiol. Lett. 56, 53–60
32) Fujiwara et al. (1992) Appl. Environ. Microbiol. 58, 4016–4025
33) Nagasaka et al. (1995) EMBL Data Library
34) Maniak et al. (1990) Nucleic Acids Res. 18, 3211–3217
35) Berka et al. (1992) EMBL Data Library
36) Joutsjoki et al. (1992) FEMS Microbiol. Lett. 78, 237–244
37) Vainio et al. (1993) Curr. Genet. 24, 38–44
38) Fagerstrom et al. (1990) J. Gen. Microbiol. 136, 913–920
39) Binder et al. (1986) Gene 47, 269–277
40) Stone et al. (1989) Curr. Genet. 24, 205–211
41) Koh-Laur et al. (1989) Enzym. Microb. Technol. 11, 692–695
42) Zhoe et al. (1989) FEBS Lett. 255, 37–41
43) Shida et al. (1991) Biosci. Biotechnol. Biochem. 56, 76–80
44) Fujita et al. (1989) J. Bacteriol. 171, 1333–1339
45) Vigal et al. (1991) Mol. Gen. Genet. 225, 278–288
46) Long et al. (1987) J. Bacteriol. 169, 5745–5754
47) Virolle et al. (1988) Gene 74, 321–334
48) Petricek et al. (1992) Gene 112, 77–83
49) Bahl et al. (1991) Appl. Environ. Microbiol. 57, 1554–1559
50) Kitamoto et al. (1988) J. BacterioL 170, 5848–5854

TABLE 5

Sources of polysaccharide binding domains

| Binding Domain | Proteins Where Binding Domain is Found |
|---|---|
| Cellulose Binding Domains[1] | β-glucanases (avicelases, CMCases, cellodextrinases)<br>exoglucanses or cellobiohydrolases<br>cellulose binding proteins<br>xylanases<br>mixed xylanases/glucanases<br>esterases<br>chitinases<br>β-1,3-glucanases<br>β-1,3-(β-1,4)-glucanases<br>(β-)mannanases<br>β-glucosidases/galactosidases<br>cellulose synthases (unconfirmed) |
| Starch/Maltodextrin Binding Domains | α-amylases[2,3]<br>β-amylases[4,5]<br>pullulanases<br>glucoamylases[6,7]<br>cyclodextrin glucotransferases[8–10]<br>(cyclomaltodextrin glucanotransferases)<br>maltodextrin binding proteins[11] |
| Dextran Binding Domains | (Streptococcal) glycosyl transferases[12]<br>dextran sucrases (unconfirmed)<br>Clostridial toxins[13,14]<br>glucoamylases[6]<br>dextran binding proteins |
| β-Glucan Binding Domains | β-1,3-glucanases[15,16]<br>β-1,3-(β-1,4)-glucanases (unconfirmed)<br>β-1,3-glucan binding protein[17] |
| Chitin Binding Domains | chitinases<br>chitobiases<br>chitin binding proteins<br>(see also cellulose binding domains)<br>Heivein |

[1]Gilkes et al., Adv. Microbiol Reviews, (1991) 303–315.
[2]S?gaard et al., J. Biol. Chem. (1993) 268:22480.
[3]Weselake et al., Cereal Chem. (1983) 60:98.
[4]Svensson et al., J. (1989) 264:309.
[5]Jespersen et al., J. (1991) 280:51.
[6]Belshaw et al., Eur. J. Biochem. (1993) 211:717.
[7]Sigurskjold et al., Eur. J. Biochem. (1994) 225:133.
[8]Villette et al., Biotechnol. Appl. Biochem. (1992) 16:57.
[9]Fukada et al., Biosci. Biotechnol. Biochem. (1992) 56:556.
[10]Lawson et al., J. Mol. Biol. (1994) 236:590.
[14]von Eichel-Streiber et al., Mol. Gen. Genet. (1992) 233:260.
[15]Klebl et al., J. Bacteriol. (1989) 171:6259.
[16]Watanabe et al., J. Bacteriol. (1992) 174:186.
[17]Duvic et al., J. Biol. Chem. (1990): 9327.

Once the most appropriate polysaccharide binding peptide for a particular application has been identified, the polysaccharide binding protein or domain can be prepared by transforming into a host cell a DNA construct comprising DNA encoding the appropriate polysaccharide binding moiety. The phrase "polysaccharide binding peptide" intends an amino acid sequence which comprises at least a functional portion of the polysaccharide binding region of a polysaccharidase or a polysaccharide binding protein. The phrase further relates to glycoprotein derivatives of such amino acid sequences. By "functional portion" is intended an amino acid sequence which binds to an oligosaccharide polymer of interest.

The techniques used in isolating polysaccharidase genes, such as a cellulase gene, and genes for polysaccharide binding proteins are known in the art, including synthesis, isolation from genomic DNA, preparation from cDNA, or combinations thereof. (See, U.S. Pat. Nos. 5,137,819; 5,202, 247; and 5,340,731) The sequences for several polypeptide binding domains, which bind to soluble oligosaccharides are known (See, FIG. 1 of PCT/CA97/00033, WO 97/26358). The DNAs coding for a variety of polysaccharidases and polysaccharide binding proteins are also known. Various techniques for manipulation of genes are well known, and include restriction, digestion, resection, ligation, in vitro mutagenesis, primer repair, employing linkers and adapters, and the like (see Sambrook et al., Molecular Cloning, A Laboratory Manual, Cold Spring Harbor Laboratory, Cold Spring Harbor, N.Y., 1989).

The amino acid sequence of a polysaccharidase also can be used to design a probe to screen a cDNA or a genomic library prepared from mRNA or DNA from cells of interest as donor cells for a polysaccharidase gene or a polysaccharide binding protein gene. By using the polysaccharidase cDNA or binding protein cDNA or a fragment thereof as a hybridization probe, structurally related genes found in other microorganisms can be easily cloned. Particularly contemplated is the isolation of genes from organisms that express polysaccharidase activity using oligonucleotide probes based on the nucleotide sequences of genes obtainable from an organism wherein the catalytic and binding domains of the polysaccharidase are discrete, although other polysaccharide binding proteins also can be used (see, for example, Shoseyov, et al., Proc. Nat'l. Acad. Sci. (USA) (1992) 89:3483–3487).

Probes developed using consensus sequences for the binding domain of a polysaccharidase or polysaccharide-binding protein are of particular interest. The β-1,4-glycanases from *C. fimi* characterized to date are endoglucanases A, B, C and D (CenA, CenB, CenC and CenD, respectively), exocehobiohydrolases A and B (CbhA and CbhB, respectively), and xylanases A and D (Cex and XylD, respectively) (see Wong et al. (1986) Gene, 44:315; Meinke et al. (1991) J. Bacteriol., 173:308; Coutinho et al., (1991) Mol. Microbiol. 5:1221; Meinke et al., (1993) Bacteriol., 175:1910; Meinke et al., (1994) Mol. Microbiol., 12:413; Shen et al., Biochem. J., in press; O'Neill et al., (1986) Gene, 44:325; and Millward-Sadler et al., (1994) Mol. Microbiol., 11:375). All are modular proteins of varying degrees of complexity (FIG. 1), but with two features in common: a catalytic domain (CD) and a cellulose-binding domain (CBD) which can function independently (see Millward-Sadler et al., (1994) Mol. Microbiol., 11:375; Gilkes et al., (1988) J. Biol. Chem., 263:10401; Meinke et al., (1991) J. Bacteriol., 173:7126; and Coutinho et al., (1992) Mol. Microbiol., 6:1242). In four of the enzymes, CenB, CenD, CbhA and CbhB, fibronectin type III (Fn3) repeats separate the N-terminal CD from the C-terminal CBD. The CDs of the enzymes come from six of the families of glycoside hydrolases (see Henrissat (1991) Biochem. J., 280:309; and Henrissat et al., (1993) Biochem. J., 293:781); all of the enzymes have an N- or C-terminal CBD or CBDs (see Tomme et al., Adv. Microb. Physiol., in press); CenC has tandem CBDs from family IV at its N-terminus; CenB and XylD each have a second, internal CBD from families III and II, respectively. Cex and XylD are clearly xylanases; however, Cex, but not XylD, has low activity on cellulose. Nonetheless, like several other bacterial xylanases (see Gilbert et al., (1993) J. Gen. Microbiol., 139:187), they have CBDs. *C. fimi* probably produces other β-1,4-glycanases. Similar systems are produced by related bacteria (see Wilson (1992) Crit. Rev. Biotechnol., 12:45; and Hazlewood et al., (1992) J. Appl. Bacteriol., 72:244). Unrelated bacteria also produce glycanases; *Clostridium thermocellum*, for example, produces twenty or more β-1,4-glycanases (see Beguin et al., (1992) FEMS Microbiol. Lett., 100:523). For solid phase recovery systems, CBDs that bind insoluble polysaccharides are of particular use. For use in phase separation purification of growth factor conjugates, a particularly useful CBD is the binding domain of *C. fimi* endoglucanase C N1, which is the only protein known to bind soluble cellosaccharides and one of a small set of proteins that are known to bind any soluble polysaccharides.

Examples of suitable binding domains are shown in FIG. 1 of PCT/CA97/00033 (WO 97/26358), which presents an alignment of binding domains from various enzymes that bind to polysaccharides and identifies amino acid residues that are conserved among most or all of the enzymes. This information can be used to derive a suitable oligonucleotide probe using methods known to those of skill in the art. The probes can be considerably shorter than the entire sequence but should at least be 10, preferably at least 14, nucleotides in length. Longer oligonucleotides are useful, up to the fall legnth of the gene, preferably no more than 500, more preferably no more than 250, nucleotides in length. RNA or DNA probes can be used. In use, the probes are typically labeled in a detectable manner, for example, with $^{32}$p, $^3$H, biotin, avidin or other detectable reagents, and are incubated with single-stranded DNA or RNA from the organism in which a gene is being sought. Hybridization is detected by means of the label after the unhybridized probe has been separated from the hybridized probe. The hybridized probe is typically immobilized on a solid matrix such as nitrocellulose paper. Hybridization techniques suitable for use with oligonucleotides are well known to those skilled in the art. Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

Generally, the binding domains identified by probing nucleic acids from an organism of interest will show at least about 40% identity (including as appropriate allowances for conservative substitutions, gaps for better alignment and the like) to the binding region or regions from which the probe was derived and will bind to a soluble β-1,4 glucan with a $K_a$ of $\geq 10^3$ M$^{-1}$. More preferably, the binding domains will be at least about 60% identical, and most preferably at least about 70% identical to the binding region used to derive the probe. The percentage of identity will be greater among those amino acids that are conserved among polysaccharidase binding domains. Analyses of amino acid sequence comparisons can be performed using programs in PC/Gene (IntelliGenetics, Inc.). PCLUSTAL can be used for multiple sequence alignment and generation of phylogenetic trees.

In order to isolate the polysaccharide binding protein or a polysaccharide binding domain from an enzyme or a cluster enzymes that binds to a polysaccharide, several genetic approaches can be used. One method uses restriction enzymes to remove a portion of the gene that codes for portions of the protein other than the binding portion thereof. The remaining gene fragments are fused with expression control sequences to obtain a mutated gene that encodes a truncated protein. Another method involves the use of exonucleases such as Bal31 to systematically delete nucleotides either externally from the 5' and the 3' ends of the DNA or internally from a restricted gap within the gene. These gene deletion methods result in a mutated gene encoding a shortened protein molecule which can then be evaluated for substrate or polysaccharide binding ability. Appropriate substrates for evaluating binding activity include those for the enzymes are listed in Tables 1–5 above, as well as the carbohydrates listed in Table 6 below.

TABLE 6

| Uncharged Polysaccharides* | Charged Polysaccharides | Low Molecular Weight Compounds |
|---|---|---|
| Dextran | Na carboxymethyl dextran | Dextrins derived from cellulose (Cellotriose, cellotetraose, etc.) |
| Hydroxypropyl dextran | Na carboxymethyl xylotriose, etc. | Xylose, xylobiose, cellulose |
| Carboxymethyl dextran | Na dextran sulfate | Maltodextrins and derivatives |
| Maltodextrin | DEAE dextran | |
| Arabinogalactan | Polygalacturonic acid (pectin) | |
| Hydroxypropyl starch | | |
| Amylopectin | | |
| Methyl cellulose | | |
| Hydroxyethyl cellulose | | |
| Ethylhydroxyethyl cellulose | | |
| Carboxymethyl cellulose | | |
| Hydroxypropyl cellulose | | |
| Ficoll | | |
| Carboxymethyl starch | | |
| Hydroxyethyl starch | | |
| Pullulan | | |
| Chitin | | |

* Polymers can be crude or purified.

Any number of affinity moieties (one and more) can be employed in the affinity complex to affinity adsorb a particulate to a solid matrix from which it is thereafter released using the method according to the present invention. For example, an antibody specific to the particulate can be used as a single moiety that affinity adsorbs the particulates to the solid matrix.

In this case the antibody is preferably first immobilized to the solid matrix (e.g., covalently) and the particulate it thereafter affinity adsorbed thereto. Methods of immobilizing an antibody to a solid matrix are well known in the art. A conjugate of an antibody and a matrix binding peptide can similarly be employed. In this case the matrix binding peptide serves to affinity immobilize the antibody to the solid matrix. A conjugate of an antibody and biotin can be employed to affinity adsorb the particulates to an avidin or streptavidin coated solid matrix. Additional combinations are envisaged. For example, a conjugate or a fusion protein of a polysaccharide binding peptide and a ligand, such as, but not limited to a growth factor can be employed. For more descriptions of cellulose binding fusion proteins, see U.S. Pat. No. 5,137,819 issued to Kilburn el al., and U.S. Pat. No. 5,719,044 issued to Shoseyov et al. and PCT/CA97/00033 (WO 97/26358) all are incorporated by reference herein. The affinity complex can include more than two moieties as desired. Based on the list of affinity moieties herein provided, and additional moieties one ordinarily skilled in the art can is design affinity complexes having any desired number of moieties. A shared characteristic to all of these moieties is that they are capable of affinity adsorbing the particulates of choice on one hand and be immobilized, either covalently or by other strong interactions to the solid matrix.

According to presently preferred embodiments of the invention the solid matrix includes a polysaccharide and the degrading enzyme is therefore a polysaccharidase. Examples of a variety of polysaccharidases are provided in Tables 1–5 above, whereas some examples of suitable polysaccharide matrices are provided in Table 6 above. Presently preferred polysaccharides include cellulosic material, agaroses, chitins, starches and derivatives thereof. Presently preferred polysaccharidases therefore include cellulases, agarases (see U.S. Pat. No. 5,869,310. Agarase isolated from Pseudomonas atlantica can be purchased from a large number of national suppliers, such as the New England Biolabs Corporation (Beverly, Mass.). Additionally, a commercially-available agarase isolated from an unknown organism can be purchased from Epicentre Technologies (Madison, Wis.). See also, Bacterial agarases, Proc. of the 7th International Seaweed Symp., (1971), pp. 469–472. In addition, Pseudomonas, Vibrio, Cytophaga, and Alteromonas genera are all known to produce agarases), chitinases and amylases, respectively. Both crude and highly purified preparations of the polysaccharide matrices and/or polysaccharidases can be used. The polysaccharidase employed should match the polysaccharide matrix and can be isolated from a natural source or be a purified or crude recombinant protein. An example for the use of agarose and agar as solid matrices for the capturing of cells is provided by Margel et al. (Margel, et al. J. Cell Biol. 1983, 62:149–159), U.S. Pat. Nos. 4,861,705 and 4,732,811, for the separation of T and B cells from heterogeneous populations of spleen cells using anti-Thy 1.2 anti-immunoglobulin antibodies or soybean agglutinin coupled to agarose-polyacrolein microsphere beads. However, the solid matrix can also be a proteinaceous matrix, e.g., a collagenous solid matrix, gelatin solid matrix, or a fibronectin solid matrix which are degradable by suitable degrading enzyme, e.g., collagenase, gelatinase or other proteases.

According to other preferred embodiments of the present invention the solid matrix is selected from the group consisting of a fabric, threads, beads and a sponge. According to a preferred embodiment the solid matrix is a polysaccharide material, preferably a cellulosic material. Thus, the polysaccharide material can be in any of a variety of forms, for example, but not limited to, crystalline cellulose, such as AVICELL™ (FMC Corp., Philadelphia, Pa.), porous and non-porous cellulose beads and bacterial microcrystalline cellulose; a mix of crystalline and amorphous cellulose such as cellulose sponges, cotton fibers or "balls", and cotton or cellulose gauze; or amorphous cellulose such as phosphoric acid swollen cellulose and other solid matrices coated with cellulose or cellulose derivatives such as cellulose acetate or ethyl hydroxyl ethyl cellulose ("EHEC"), etc. The chitin material can be, for example, but not limited to, granular chitin from crab shells (Sigma Chemical Co., St. Louis, Mo.) or chitin beads. Most preferably, the cellulosic, chitin or other matrix is a material that will not clog upon filtering large volumes of sample therethrough.

The particulates according to the present invention can be either viruses, cells or portions thereof. The cells can be either prokaryotic or eukaryotic cells. Eukaryotic cells include, for example, growth factor dependent cells, fetal cells, bone marrow derived cells, blood derived cells and tumor derived cells. Additional examples includes eukaryotic microorganisms, such as yeast, fungi, protozoan and nematode cells. Prokaryote cells include, for example, pathogenic and non-pathogenic bacteria. Microorganisms that can be released and detected using the method of the present invention include, but are not limited to, bacteria, viruses, fungi, protozoans, and nematodes. For example, the bacteria can be *Escherichia coli*, Salmonella, Campylobacter, Legionella, Clostridium, Pseudomonas, Listeria, Staphylococcus, Bacillus, Shigella, Mycobacteria, Bordetella, Streptococcus, etc. The viruses include, for example, but are not limited to, viruses of the families: Poxviridae, Iridoviridae, Herpesviridae, Adenoviridae, Papovarviridae, and Retroviridae, such as the Acquired Immune Deficiency Syndrome (AIDS) virus, etc. Fungi which can be released by the method of the present invention include, for example, Aspergillus, Blastomyces, Candida (such as yeast), Coccidioides, Cryptococcus and Histoplasma, etc. The protozoan groups that can be released by the method of the present invention include, for example, Rhizopoda (e.g., amoeba such as *Entamoeba histolytica*, and Dientamoeba fragilis), Mastigophora (flagellates) (e.g., *Giardia larablia*), Ciliatea (ciliates, e.g., *Balantidium coli*) and Sporozoa (e.g., Isospora, Cryptosporidium). For further examples of microorganisms, see, Microbiology, 4th ed., Davis et al., 1990, J.B. Lippincott Co., Philadelphia, Pa.; and Fundamental Cytology, 3rd ed., 1996, Lippencott-Raven Publishers, Philadelphia, PA. See also, Zinsser Microbiology 19th ed., Joklik et al., 1988, Appleton & Lange, Norwalk, Conn., or any other available textbook on microbiology available to those skilled in the art.

Once the particulates have been released from the solid matrix to which they were adsorbed by the action of the degrading enzyme which degrades the solid matrix, the particulates can be physically removed (eluted or separated) from the solid matrix. Thus, if the solid matrix is arranged in a column, the particulates are eluted therefrom via the addition of an appropriate liquid at the top of the column. Such a liquid can include a buffer, e.g., an isotonic buffer such as buffered saline, or a growth medium. If, on the other hand, the solid matrix is in dispersion, a simple step of, for example, centrifugation or filtration can be used to separate the matrix and the particulates that have been released therefrom. The removed particulates can thereafter be recovered by plating into or on a suitable growth medium. The type of growth medium required to recover and sustain specific particulates depend to a great extent on the particulates of choice. One ordinarily skilled in the art would know how to select an appropriate growth medium to recover specific particulates.

The use of a matrix degrading enzyme to release solid support adsorbed particulates therefrom is introduced herein for the first time and renders the method according to the present invention highly universal. Thus, regardless of the method employed to capture or adsorb the particulates, the matrix degrading enzyme ensures the release of the particulates therefrom. In addition, it will be appreciated that the method according to the present invention dissociated the particulates from the matrix at a location which is as far as possible from the particulates, using highly specific degrading enzymes which do not affect the particulates themselves. As such, the method according to the present invention ensures that a minimal damage, if any, is inflicted upon the particulates when released. While reducing the present invention to practice an unexpected phenomenon has been observed, i.e., non-stoichiometric amounts of the degrading enzyme were sufficient to release a high fraction of the adsorbed particulates, close to 100% thereof in some cases. This phenomenon is explained, in a non-limiting fashion, by that the degrading enzymes degrade the surface of the solid matrix which is sufficient to release the particulates therefrom. By "non-stoichiometric amounts" is meant amounts which are insufficient to degrade the entire solid matrix. In fact, close to 100% release was experienced while macroscopically the matrix itself appeared unchanged. Support for the surficial action of cellulases can be found in a large pool of prior art documents which are related to the treatment of cellulose made fabrics by cellulases (U.S. Pat. Nos. 5,824,115; 5,821,358; 5,811,381; 5,770,104; 5,759,210; 5,709,116; 5,707,858; 5,700,686; 5,588,290; 5,677,151; 5,668,073; 5,668,009; 5,654,193 5,650,322 and others which are uncovered by searching the U.S. full text patents database with the key words "cellulase treatment").

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

EXAMPLE 1

Elution of Microorganisms Which Have Been Captured by a CBD-antibody Using Cellulase The following example demonstrates that microorganisms which have been selectively captured onto a cellulose matrix by a CBD-antibody affinity complex can be released and thereafter eluted from the matrix and recovered by incubating the CBD-receptor-microorganism-matrix complex with a cellulase.

Materials and Experimental Methods:

Release and elution buffers:

1. 89 Units/ml (10 mg/ml) *Trichoderma viride* cellulase (Sigma Cat. No. C-9422, Lot No. 35H0403) in 0.1 M acetate buffer, pH 5.0.

2. 890 Units/ml (100 mg/ml) *Trichoderma viride* cellulase (Sigma Cat. No. C-9422, Lot No. 35H0403) in 0.1 M acetate buffer, pH 5.0.

3. 95 Units/ml (10 mg/ml) *Penicillium funiculosum* cellulase (Sigma Cat. No. C-0901) in 0.1 M acetate buffer, pH 5.0.

4. 950 Units/ml (100 mg/ml) *Penicillium funiculosum* cellulase (Sigma Cat. No. C-0901) in 0.1 M acetate buffer, pH 5.0.

5. 0.1 M acetate buffer, pH 5.0, which was used as control.

Preparation of a CBD-IC capture cartridge:

50 mg cotton gauze was packed into a CBD-IC cartridge and then 150 µl of a solution containing CBD-anti *E. coli* O157:H7 conjugate in PBS-Tween (0.05%) was loaded into the cartridge.

Capture and wash step:

1 ml of PBS containing 185 CFU's *E. coli* O157:H7 was passed through the CDB-IC cartridge by a single gravity pass resulting in approximately 50% capture, or 95 CFU's. Following the capture step, the cartridge was washed with 10 ml PBS-Tween (0.05%) and 10 ml PBS.

Release step:

In order to elute the captured bacteria from the matrix, two different types of cellulase were tested, *Trichoderma viride* cellulase and *Penicillium funiculosum* cellulase. 200 μl of a cellulase solution containing 10 or 100 mg cellulase per ml, i.e., 18 or 180 units per cartridge and 19 or 190 units per cartridge for *Trichoderma viride* cellulase and *Penicillium funiculosum* cellulase, respectively, were drawn into their respective cartridges and incubated for 30 minutes at 37° C. to release the affinity adsorbed bacteria from the matrix.

Eluting and plating of microorganisms:

Following the incubation with cellulase, the eluant was drawn three times in and out of cartridge before being expelled from the cartridge and plated onto mEndo LES agar plates for quantification of bacterial CFU's. The first elution was followed by 200 μl PBS eluant which was drawn in and out of cartridge three times before being expelled and plated onto mEndo LES agar for quantification of bacterial CFU's. Finally, certain cartridges which were treated with 100 mg/ml cellulase were eluted with an additional 10 ml PBS-Tween and 10 ml PBS to determine if any additional microorganisms had been released but not removed from the cartridge by previous eluants. These solutions were quantified for CFU's using the mEndo Les agar filtration technique by filtering the eluant through GN-6 filter and then plating the filter on mENDO LES agar for viable cell count. Cellulase buffer (0.1 M acetate buffer, pH 5.0) was used as a control. In addition, the gauze itself was plated onto mENDO LES agar where indicated.

Experimental Results:

*Trichoderma viride* cellulase (C-9422) was more suitable for the elution of CBD immunocaptured bacteria than *Penicillium funiculosum* cellulase (C-0901), effecting nearly 100% elution as compared to 70%, respectively, when the higher cellulase concentrations were used (FIG. 1). Cartridges in which 100 mg/ml *Trichoderma viride* cellulase eluant was used and in which 10 ml PBS-Tween and 10 ml PBS wash steps were incorporated resulted in only two colonies remaining on the gauze and >50% of the loaded microorganisms, 100 CFUs, were eluted in the combined elution and wash steps demonstrating that nearly 100% of the captured *E. Coli* O1 57:H7 bacteria were eluted and recovered.

These results show that cellulase can be used to elute microorganisms which have been captured to cellulose matrix without any detrimental effects on the viability of the microorganisms. This can be achieved using cellulose originating from different microorganisms, such as, but not limited to, *Trichoderma viride* and *Penicillium funiculosum*. Between these two cellulases, *Trichoderma viride* cellulase is presently the preferred cellulase, using which, 200 μl of 100 mg/ml solution was sufficient to effect nearly 100% elution of viable captured *E. coli* O157:H7 from the matrix.

EXAMPLE 2

Elution of Ground Beef Extract Derived Microorganisms Which Have Been Captured by a CBD-antibody Using Cellulase The following example demonstrates that low levels of pathogenic microorganisms which have been captured onto a cellulose matrix via a CBD-antibody from food samples containing large heterogeneous populations of non-pathogenic microorganisms can be eluted from the matrix by incubating the CBD-antibody-microorganism-matrix complex with cellulase.

Materials and Experimental Methods:

Release and elution buffers:

1. 890 Units/ml (100 mg/ml) *Trichoderma viride* Cellulase (Sigma Cat. No. C-9422, Lot No. 35H0403 8.9 Units per mg) in 0.1 M acetate buffer, pH 5.0.

2. 0.1 M acetate buffer, pH 5.0, which was used as control.

Preparation of a CBD-IC capture cartridges:

50 mg cotton gauze was packed into each cartridge and then 150 μl of a solution containing CBD-anti *E. coli* O157:H7 conjugate in PBS-Tween (0.05%) was loaded into the cartridge.

Capture and wash step:

225 ml PBS was added to 25 grams of ground beef which was then stomached for one minute using a Seward 400 stomacher. The stomached beef sample was then filtered through a cotton filter (Spuntech™ cotton) and the extract was inoculated with 0 CFU, 211 CTJ's or 1055 CFUs *E. coli* O157:H7 and then passed through the cartridges by a gravity pass over 30 minutes. Following the capture step, the cartridge was washed once with 5 ml of PBS-Tween (0.05%) from bottom up followed by expulsion of the wash fluid. Then 10 ml PBS-Tween (0.05%) and 10 ml of PBS were used to wash the cartridge from top to bottom.

Release step:

200 μl of cellulase solution containing 100 mg cellulase per ml, 180 units per CBD-IC cartridge, were drawn into the cartridge and then incubated for 30 minutes at 37° C. to release the bacteria from the matrix. Following the incubation, the eluant was drawn once up and down in the cartridge and then expelled from the cartridge and plated onto CT-SMAC agar and was incubated overnight at 37° C. for quantification and identification of bacterial CFU's. CT-SMAC is selective for *E. coli* O157:H7, which is sorbitol negative and is resistant to cefixime and tellurite (CT). Enzyme buffer (0.1 M acetate buffer, pH 5.0) was used as a control eluant.

Figure 2:
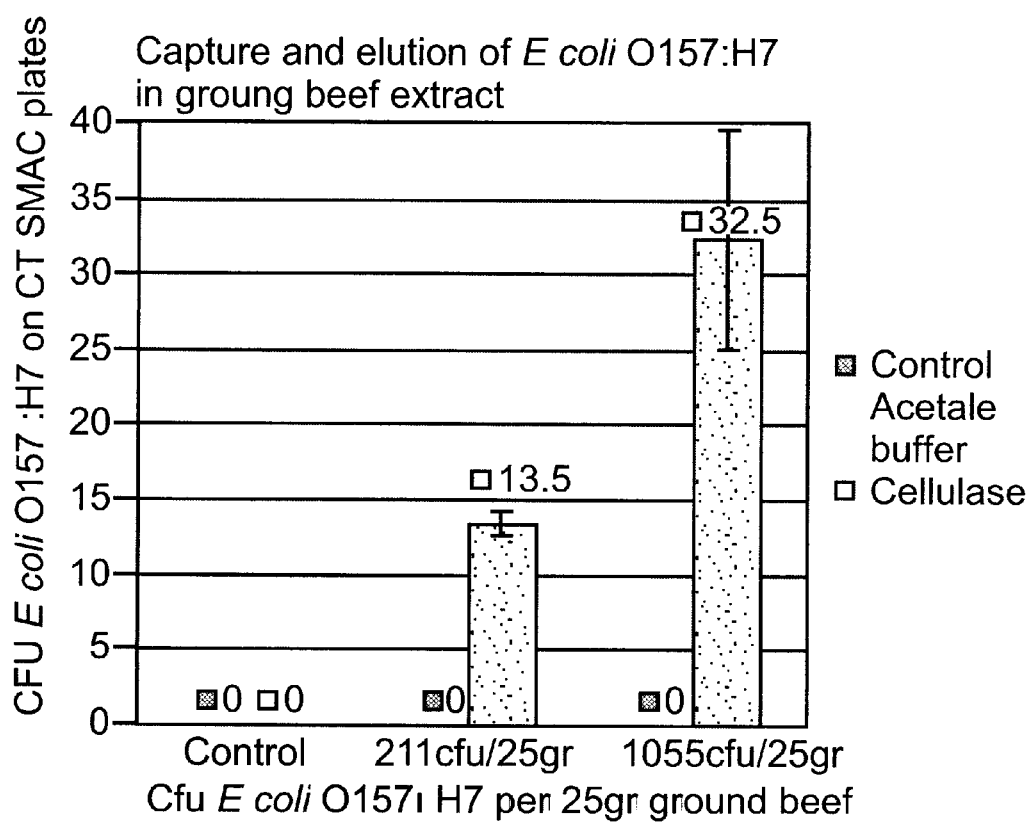
FIG. 2 demonstrates elution of *E. coli* O157:H7 immunoconcentrated with CBD-IC from ground beef extract using cellulase. CBD-IC cartridges were used to capture viable *E. coli* O157:H7 cells from 250 ml ground beef extract containing 211 CFU's or 1055 CFU's *E. coli* O157:H7. Following capture and wash steps, each cartridge was incubated for 30 minutes with a cellulase solution to release and elute viable bacteria which were then plated onto CT-SMAC agar for quantification of CFU's and identification of presumptive *E. coli* O157:H7 positives. Each bar indicates the number of *E. coli* O157:H7 bacteria eluted and recovered in a viable form on CT-SMAC plates from the 200 µl cellulase eluant.

Experimental Results:

Sorbitol negative colonies appeared on CT-SMAC plates inoculated with eluants from the meat samples but not from control meat samples which were not inoculated with *E. coli* O157:H7 (FIG. 2). Sorbitol negative colonies were easily identified due to the extremely low background on the CT-SMAC plates. All plates contained between 1–10 colonies which were sorbitol positive resulting in easily identifiable sorbitol negative colonies. Ten sorbitol negative colonies were chosen randomly from the CT-SMAC plates and tested with the Oxoid *E. coli* O157 latex kit. All ten colonies tested resulted in *E. coli* O157 positive agglutination.

These results demonstrate that cellulose can be used to capture low levels of pathogenic microorganisms from food samples containing large heterogeneous populations of non-pathogenic microorganisms and then specifically elute the target microorganisms from the matrix by incubating the CBD-antibody-microorganism-matrix complex with cellulase. Due to the high specificity of the cellulose matrix and the effective wash step prior to elution, the elution step results in high target to background ratio as can be seen on CT-SMAC agar plates in which most colonies are Sorbitol negative and *E. coli* O157 positive.

EXAMPLE 3

Elution of Microorganisms Which Have Been Captured by a MBP-antibody Using α-amylase The following example demonstrates that microorganisms which have been selectively captured onto an amylose coated matrix by a maltose binding protein (MBP)-antibody affinity complex can be released and thereafter eluted from the matrix and recovered by incubating the MBP-receptor-microorganism-matrix complex with a α-amylase.

Materials and Experimental Methods:

Release and elution buffers:

1. 79000 Units/ml (100 mg/ml) *Bacillus licheniformis* α-amylase (Sigma Cat. No. A-4551, Lot No. 45H8075) in PBS buffer, pH 7.2.

2. 4000 Units/mil (100 mg/ml) *Aspergillus oryzae* α-amylase (Sigma Cat. No. A-0273, Lot No. 84H1185) in PBS buffer, pH 7.2.

3. PBS buffer, pH 7.2, which was used as control.

Preparation of an immunoconcentrator (IC) using Maltose Binding Protein (MBP):

SPDP conjugation procedure:

Materials: MBP2*—Maltose Binding Protein-New England Biolabs, Inc. Product No. 800-44L. IgG, KPL affinity purified antibody goat anti-*E. coli* O157:H7, Cat. No. 95-90-10, Lot No. TH077. SPDP; N-Succinimidyl 3-(2-pyridyldithio) propionate (SPDP, Mw 312.4 g/mol), Cat. P-3415, Sigma. Amylose (from corn), practical grade—approximately 70%, Cat. No. A-7043, Sigma. α-amylase from Bacillus licheniformis, Cat. No. A-4551, Lot No. 45H8075, Sigma. α-amylase from *Aspergillus oryzae*, Cat. No. A-0273, Lot No. 84H1185, Sigma.

Method: In two separate reactions, 1.8 mg MBP (6.0 mg/ml) was mixed with 20-fold molar excess of SPDP (68 mM solution dissolved in ethanol) and 2.2 mg IgG (1.5 mg/ml) was mixed with 25-fold molar excess of SPDP (68 mM solution dissolved in ethanol). Both of these reactions were allowed to continue for two hours at room temperature. The reactions were then dialyzed against PBS overnight at 4° C. and the precipitates were collected by centrifugation.

IgG was reduced by addition of 1 M DTT to a final concentration of 50 mM and incubation for 1 hour at room temperature. The reduced IgG was desalted on a G-25 column (up to 5% sample/column volume ratio) by equilibration with 50 mM $KH_2PO_4$ pH 6.5. The reduced SPDP-IgG was then mixed with the SPDP-MBP in a molar ratio of 1:2.9, respectively, at 4° C. over night. The precipitates were removed by centrifugation and the supernatant was stored at 4° C.

Preparation of amylose coated gauze matrix:

1.3 grams amylose were mixed with 100 ml distilled water and the mixture was brought to boil. 50 mg pre-cut gauze quadrants were added to the boiling amylose solution and the amylose coated gauze was removed after 1–2 minutes from the boiling solution and was air dried at room temperature. Excess amylose was washed from the gauze quadrants by stirring the coated gauze in 1 liter Tris buffer, pH 7.4, at 60° C. for 5 minutes. The wash step was repeated two more times using fresh Tris buffer. Finally, each individual quadrant of coated gauze was washed with 1 ml Tris buffer, pH 7.4, and air dried at room temperature.

Preparation of an MBP-IC capture cartridge:

The dried gauze was then pack into a cartridge. NaCl was added to the conjugate at a final concentration of 0.2 M. 150 µl of conjugate (final concentration of 0.1 mg protein/ml as determined by the Bradford method) was added onto the packed gauze, incubated for 15 minutes at 37° C., cooled to room temperature and washed twice with 5 ml of PBS. The MBP-Ab-IC cartridge was then ready for use.

Capture and wash step:

1 ml of PBS containing 250 CFU's of *E. coli* O157:H7 was drawn into an MBP-Ab-IC cartridge or an MBP-IC cartridge by a standard action of a lab pipettor actuated 5 times in an up and down manner. Thereafter, the cartridge was washed with 10 ml of a PBS solution. The amount of captured bacteria was calculated by subtracting the amount of bacteria present in the wash solutions from original inoculum number to be approximately 46% (114 CFU's).

1 ml of expelled model solution was added to 10 ml wash and the bacterial concentration was determined by a filter method using the mENDO LES agar filtration technique. Thus, the eluant was filtered through a GN-6 Metricel filter and then the filter was plated on a mENDO LES agar and incubated overnight at 37° C. for viable cell count.

Release step:

In order to release the captured bacteria from the matrix, two different types of α-amylases were tested, *Bacillus licheniformis* α-amylase and *Aspergillus oryzae* α-amylase. To this end, 200 µl of an α-amylase solution containing 100 mg α-amylase per ml, i.e., 79000 or 4000 units per cartridge for *Bacillus licheniformis* α-amylase and *Aspergillus oryzae* α-amylase, respectively, were drawn into the cartridges and incubated for 30 minutes at room temperature to release the affinity adsorbed bacteria from the matrix.

Eluting and plating of microorganisms:

Following the incubation with α-amylase, the elution buffer was drawn three times in and out of the cartridge before being expelled from the cartridge and plated onto mENDO LES agar plates for quantification of bacterial CFUs. The first elution was followed by 200 µl PBS wash which was drawn in and out of cartridge three times before being expelled and plated onto mENDO LES agar for quantification of bacterial CFU's. Elution buffer (PBS) without α-amylase was used as a control.

Figure 3:
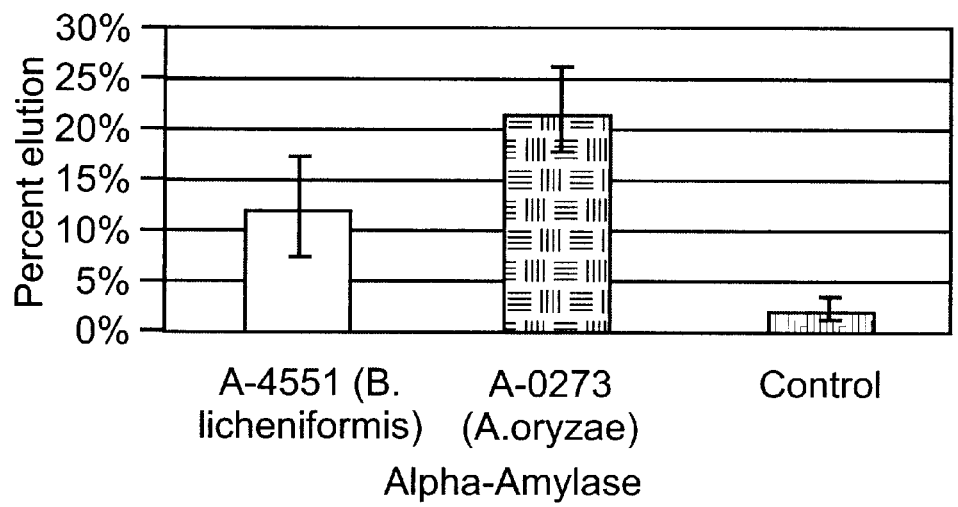
FIG. 3 demonstrates elution of *E. coli* O157:H7 immunoconcentrated with MBP-IC using α-amylase. MBP-IC Cartridge was used to capture viable *E. coli* O157:H7 cells from 1 ml PBS solution containing 250 CFU. After capture and wash steps each cartridge was incubated for 30 minutes with *Bacillus licheniformis* α-amylase, *Aspergillus oryzae* α-amylase or with PBS (control) to elute viable bacteria which were then plated on mENDO LES agar for quantification of CFU's. Bars indicate bacteria eluted in 200 µl α-amylase eluant and 200 µl PBS wash combined.

Experimental Results:

*Aspergillus oryzae* α-amylase (A-0273) was more suitable for the elution of MBP-Ab immunocaptured bacteria, than *Bacillus licheniformis* a -amylase effecting 19.2% elution as compared to 10.8%, respectively, at 100 mg α-amylase concentrations (FIG. 3). The percentages in FIG. 3 represent the CFU's which were eluted by the 200 µl eluant and the 200 µl wash step combined.

These results show that α-amylase can be used to elute microorganisms which have been captured to amylose matrix without any apparent detrimental effects on the viability of the microorganisms. This can be achieved using α-amylase originating from different microorganisms, such as, but not limited to, *Aspergillus oryzae* and *Bacillus licheniformis*. Between these two α-amylases, *Aspergillus oryzae* α-amylase is presently the preferred α-amylase, using which, 200 µl of 100 mg/ml solution was sufficient to effect nearly 20% elution of viable captured *E. coli* O157:H7 from the matrix without incorporation of large volume wash step.

EXAMPLE 4

The use of a variety of reagents has been attempted to elute viable cells which have been captured on a cellulosic matrix using CBD-antibody as the affinity complex. These included the following reagents: ethylene glycol (1–50% solutions), glycerol (50% solution), DTT (20–500 mM), glycine HCl pH 2.2–3.0+ethylene glycol, pepsin, CMC, cellobiose, $CBD_{Clos}$ (5 mg/ml), heat killed competitive antigen, KOH, and polyethylene glycol.

These reagents either had adverse effect on the viability of the cells or were unable to elute viable cells. Nevertheless, when the number of target cells was high enough on one hand and care was taken to place eluted cells in an appropriate resuscitation media immediately after elution, then it was possible to recover a small number of viable cells (in the range of 2–5%).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of releasing affinity adsorbed particulates from a solid matrix, the method comprising the step of adding to the solid matrix a degrading enzyme capable of degrading the solid matrix, to thereby release the affinity adsorbed particulates from the solid matrix, wherein said particulates are selected from the group consisting of viruses or portions thereof, cells or portions thereof and microorganisms or portions thereof, the method further comprising at least one step selected from the group consisting of eluting the particulates, recovering the particulates and separating the particulates from the solid matrix.

2. The method of claim 1, wherein the particulates are affinity adsorbed to said solid matrix via an endogenous determinant of the particulates.

3. The method of claim 2, wherein said endogenous determinant resides on a surface of said particulate and is selected from the group consisting of a complex carbohydrate, a lipopolysaccharide, a protein and a glycoprotein.

4. The method of claim 2, wherein the particulates are affinity adsorbed to said solid matrix via an affinity complex which is bound to said determinant of the particulates on one hand and to the solid matrix on the other hand.

5. The method of claim 4, wherein said affinity complex includes at least one affinity moiety selected from the group consisting of an antibody, an antigen, a hapten, a ligand, a soluble receptor, a matrix binding peptide, avidin, streptavidin and biotin.

6. The method of claim 5, wherein said ligand is selected from the group consisting of a growth factor, a hormone and a neurotransmitter.

7. The method of claim 5, wherein said soluble receptor is selected from the group consisting of a growth factor receptor, a hormone receptor and a neurotransmitter receptor.

8. The method of claim 5, wherein said matrix binding peptide is a polysaccharide binding protein.

9. The method of claim 5, wherein said matrix binding peptide is a polysaccharide binding domain.

10. The method of claim 1, wherein the solid matrix includes a polysaccharide and further wherein said degrading enzyme is a polysaccharidase.

11. The method of claim 10, wherein said polysaccharide is selected from the group consisting of a cellulosic material, an agarose, a chitin, a starch and derivatives thereof.

12. The method of claim 10, wherein said polysaccharidase is selected from the group consisting of a cellulase, an agarase, a chitinase and an amylase.

13. The method of claim 1, wherein said cells are selected from the group consisting of prokaryotic cells and eukaryotic cells.

14. The method of claim 13, wherein said prokaryotic cells are bacterial pathogens.

15. The method of claim 13, wherein said eukaryotic cells are selected from the group consisting of growth factor dependent cells, fetal cells, bone marrow derived cells, blood derived cells and tumor derived cells.

16. The method of claim 1, wherein said solid matrix is selected from the group consisting of a fabric, threads, beads, a powder, a membrane and a sponge.

17. A method of releasing growth factor dependent cells from a polysaccharide matrix to which the growth factor dependent cells being adsorbed via an affinity complex including said growth factor and a polysaccharide binding peptide, the method comprising the step of adding to the polysaccharide matrix a polysaccharidase capable of degrading the polysaccharide matrix, to thereby release the growth factor dependent cells from the polysaccharide matrix.

18. A method of releasing a microorganism from a polysaccharide matrix to which the microorganism being adsorbed via an affinity complex including a polysaccharide binding peptide-receptor conjugate specific for the microorganism, the method comprising the step of adding to the polysaccharide matrix a polysaccharidase capable of degrading the polysaccharide matrix, to thereby release the microorganism from the polysaccharide matrix.

19. A method of releasing biological particulates from a solid matrix, the method comprising the step of adding to the solid matrix a degrading enzyme capable of degrading the solid matrix, to thereby release the biological particulates from the solid matrix, wherein the solid matrix includes a polysaccharide and further wherein said degrading enzyme is a polysaccharidase.

20. The method of claim 19, wherein the biological particulates are adsorbed to said solid matrix.

21. The method of claim 19, wherein the biological particulates are affinity adsorbed to said solid matrix.

22. The method of claim 19, wherein the biological particulates are affinity adsorbed to said solid matrix via an endogenous determinant of the biological particulates.

23. The method of claim 22, wherein said endogenous determinant resides on a surface of said particulate and is selected from the group consisting of a complex carbohydrate, a lipopolysaccharide, a protein and a glycoprotein.

24. The method of claim 22, wherein the biological particulates are affinity adsorbed to said solid matrix via an affinity complex which is bound to said determinant of the biological particulates on one hand and to the solid matrix on the other hand.

25. The method of claim 24, wherein said affinity complex includes at least one affinity moiety selected from the group consisting of an antibody, an antigen, a hapten, a ligand, a soluble receptor, a matrix binding peptide, avidin, streptavidin and biotin.

26. The method of claim 25, wherein said ligand is selected from the group consisting of a growth factor, a hormone and a neurotransmitter.

27. The method of claim 25, wherein said soluble receptor is selected from the group consisting of a growth factor receptor, a hormone receptor and a neurotransmitter receptor.

28. The method of claim 25, wherein said matrix binding peptide is a polysaccharide binding protein.

29. The method of claim 25, wherein said matrix binding peptide is a polysaccharide binding domain.

30. The method of claim 19, wherein said polysaccharide is selected from the group consisting of a cellulosic material, an agarose, a chitin, a starch and derivatives thereof.

31. The method of claim 19, wherein said polysaccharidase is selected from the group consisting of a cellulase, an agarase, a chitinase and an amylase.

32. The method of claim 19, wherein said biological particulates are viruses or portions thereof.

33. The method of claim 19, wherein said biological particulates are cells or portions thereof.

34. The method of claim 33, wherein said cells are selected from the group consisting of prokaryotic cells and eukaryotic cells.

35. The method of claim 34, wherein said prokaryotic cells are bacterial pathogens.

36. The method of claim 34, wherein said eukaryotic cells are selected from the group consisting of growth factor dependent cells, fetal cells, bone marrow derived cells, blood derived cells and tumor derived cells.

37. The method of claim 19, wherein said biological particulates are microorganisms or portions thereof.

38. The method of claim 19, wherein said solid matrix is selected from the group consisting of a fabric, threads, beads, a powder, a membrane and a sponge.

39. The method of claim 19, further comprising the step of eluting the biological particulates.

40. The method of claim 19, further comprising the step of recovering the biological particulates.

41. The method of claim 19, further comprising the step of separating the biological particulates and the solid matrix.

42. A method of releasing living particulates from a solid matrix, the method comprising the steps of:

(a) adding to the solid matrix a degrading enzyme capable of degrading the solid matrix, to thereby release the living particulates from the solid matrix; and (b) recovering the living particulates.

43. A method of releasing affinity adsorbed particulates from a solid matrix, the method comprising the steps of:

(a) adding to the solid matrix a degrading enzyme capable of degrading the solid matrix, to thereby release the affinity adsorbed particulates from the solid matrix; and (b) eluting the affinity adsorbed particulates.

* * * * *